(12) United States Patent
Norling

(10) Patent No.: US 11,426,482 B2
(45) Date of Patent: Aug. 30, 2022

(54) SYSTEMS AND METHODS FOR CLEANING AND STERILIZING FLUIDS AND ARTICLES USING ELECTROMAGNETIC WAVES

(71) Applicant: Rasmus Par Tomas Norling, San Juan, PR (US)

(72) Inventor: Rasmus Par Tomas Norling, San Juan, PR (US)

( * ) Notice: Subject to any disclaimer, the term of this patent is extended or adjusted under 35 U.S.C. 154(b) by 221 days.

(21) Appl. No.: 16/387,045

(22) Filed: Apr. 17, 2019

(65) Prior Publication Data

US 2019/0314537 A1 Oct. 17, 2019

Related U.S. Application Data

(60) Provisional application No. 62/659,010, filed on Apr. 17, 2018.

(51) Int. Cl.
*A61L 2/26* (2006.01)
*A61L 2/24* (2006.01)
*A61L 2/03* (2006.01)

(52) U.S. Cl.
CPC .......... *A61L 2/26* (2013.01); *A61L 2/03* (2013.01); *A61L 2/24* (2013.01); *A61L 2202/11* (2013.01); *A61L 2202/14* (2013.01); *A61L 2202/20* (2013.01)

(58) Field of Classification Search
CPC ..... A61L 2/26; A61L 2/24; A61L 2/03; A61L 2202/11; A61L 2202/20; A61L 2202/14; A23L 3/32; C02F 1/30; C02F 1/482; C02F 2303/04; C02F 1/283
See application file for complete search history.

(56) References Cited

U.S. PATENT DOCUMENTS

| | | | |
|---|---|---|---|
| 4,719,018 A | 1/1988 | Przybylski | |
| 4,865,748 A | 9/1989 | Morse | |
| 4,974,503 A | 12/1990 | Koch | |
| 4,978,501 A | 12/1990 | Diprose et al. | |
| 5,326,445 A | 7/1994 | Binger | |
| 5,326,446 A | 7/1994 | Binger | |

(Continued)

FOREIGN PATENT DOCUMENTS

| | | |
|---|---|---|
| WO | 2014035343 A1 | 3/2014 |
| WO | 2017018944 A1 | 2/2017 |

*Primary Examiner* — Regina M Yoo
(74) *Attorney, Agent, or Firm* — Robert M. Schwartz; Kerry P. Sisselman

(57) ABSTRACT

Systems and methods are disclosed for cleaning and sterilizing fluids and other materials. In one implementation, one or more emitters are submerged within a fluid and emit electromagnetic waves having a variable frequency. The frequency of the electromagnetic waves is swept across a frequency range to neutralize bacteria, viruses, and other pathogens in the fluid. The emitters may be submerged within a fluid reservoir and/or within the interior of an enclosed fluidic path (e.g., a pipe). Solid materials may be sterilized by immersing the solid materials within the fluid of such a fluid reservoir. In another implementation, electromagnetic waves may be applied to one or more wires that are wrapped around an exterior wall of a pipe. The frequency of the electromagnetic waves may be varied across a frequency range, resulting in scale and other materials being cleaned from the interior wall of the pipe.

15 Claims, 16 Drawing Sheets

(56) References Cited

U.S. PATENT DOCUMENTS

| | | |
|---|---|---|
| 5,514,283 A | 5/1996 | Stefanini |
| 5,595,666 A | 1/1997 | Kochen et al. |
| 5,667,677 A | 9/1997 | Stefanini |
| 5,951,856 A | 9/1999 | Cho |
| 6,145,542 A | 11/2000 | Walker |
| 6,706,170 B1 | 3/2004 | De Baat Doelman |
| 6,860,990 B2 | 3/2005 | Bartl et al. |
| 6,875,360 B2 | 4/2005 | Allen et al. |
| 7,419,603 B2 | 9/2008 | Cho |
| 7,981,288 B2 | 7/2011 | Bradley et al. |
| 8,029,669 B2 | 10/2011 | Stefanini |
| 9,140,412 B2 | 9/2015 | Stefanini et al. |
| 9,181,113 B2 | 11/2015 | Clark et al. |
| 9,536,758 B1* | 1/2017 | Deo .................. A61F 7/12 |
| 2001/0035342 A1* | 11/2001 | Morse ................ C02F 1/48 204/164 |
| 2002/0049483 A1* | 4/2002 | Knowlton ........... A61N 1/403 607/101 |
| 2002/0195395 A1 | 12/2002 | Telfer et al. |
| 2005/0121396 A1 | 6/2005 | Kosakewich |
| 2007/0029261 A1 | 2/2007 | Chew |
| 2008/0128283 A1 | 6/2008 | Janse Van Rensburg |
| 2009/0084734 A1 | 4/2009 | Yencho |
| 2012/0261265 A1 | 10/2012 | Kruger |
| 2013/0153440 A9* | 6/2013 | Kanzius ............. C01B 3/042 205/687 |
| 2014/0039495 A1* | 2/2014 | Bonutti ........... A61B 17/7059 606/60 |
| 2015/0232352 A1 | 8/2015 | Chew |
| 2015/0344328 A1 | 12/2015 | Suvorov |
| 2016/0207801 A1 | 7/2016 | Stronczek |
| 2017/0252439 A1 | 9/2017 | Foo |
| 2018/0177005 A1* | 6/2018 | Guatta ................ H05B 6/687 |
| 2018/0222778 A1 | 8/2018 | Chew et al. |
| 2020/0277209 A1* | 9/2020 | Fraser ................ C02F 1/484 |

\* cited by examiner

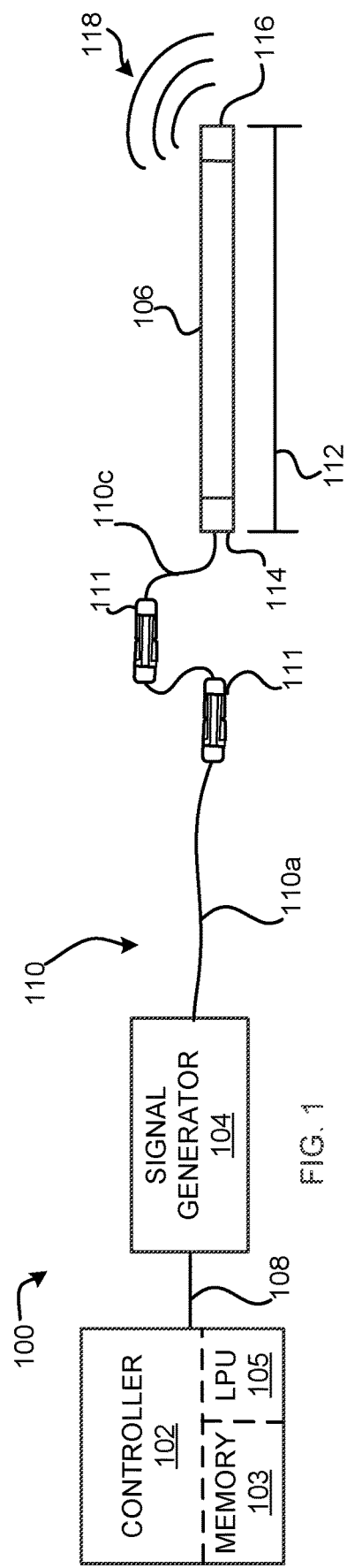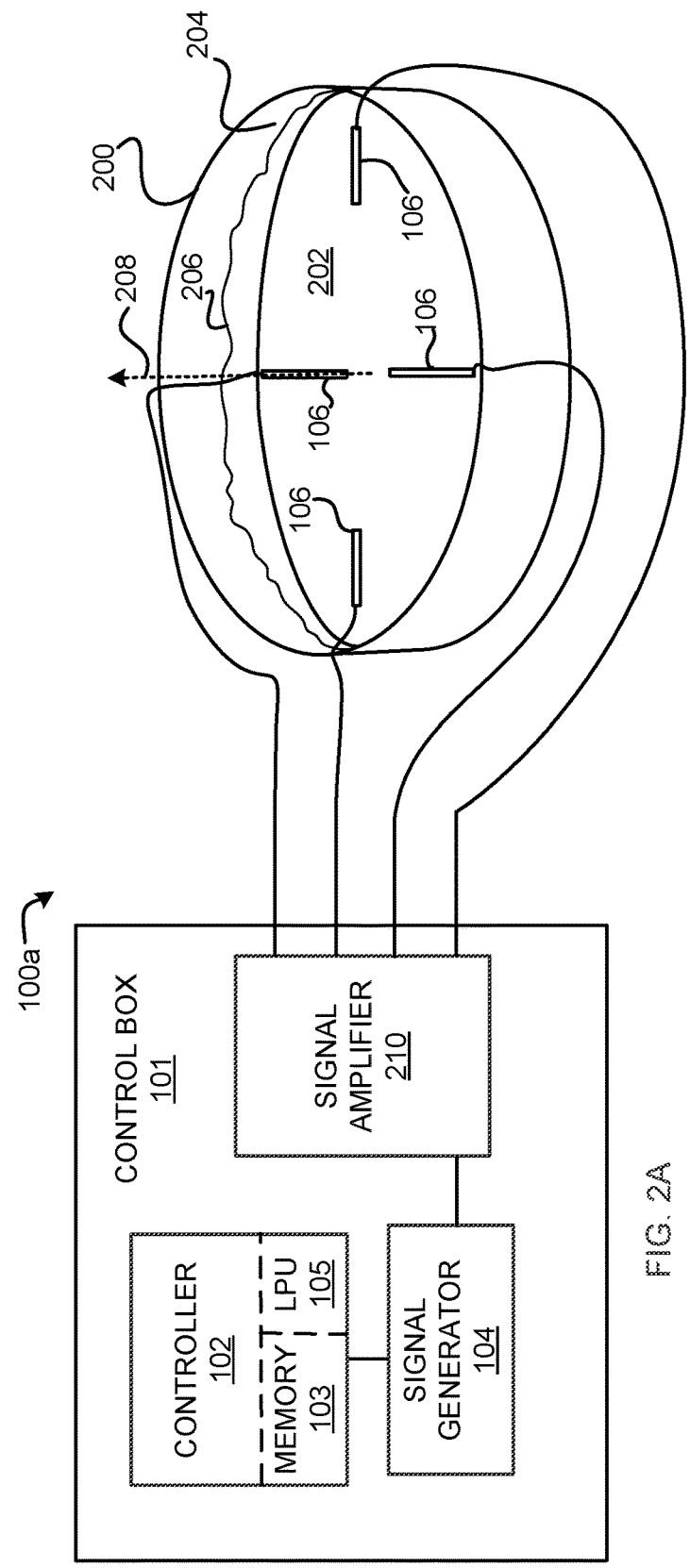

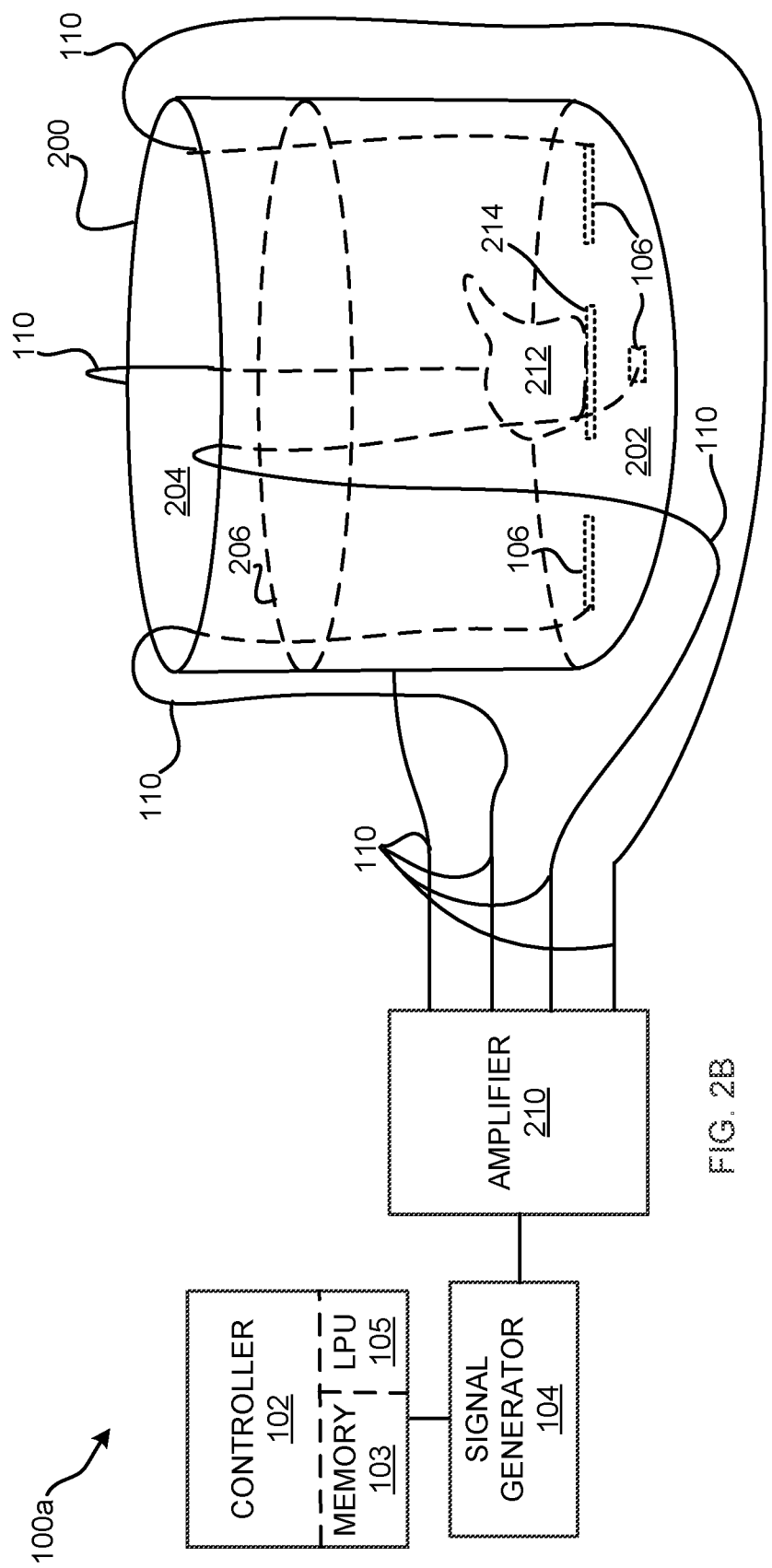

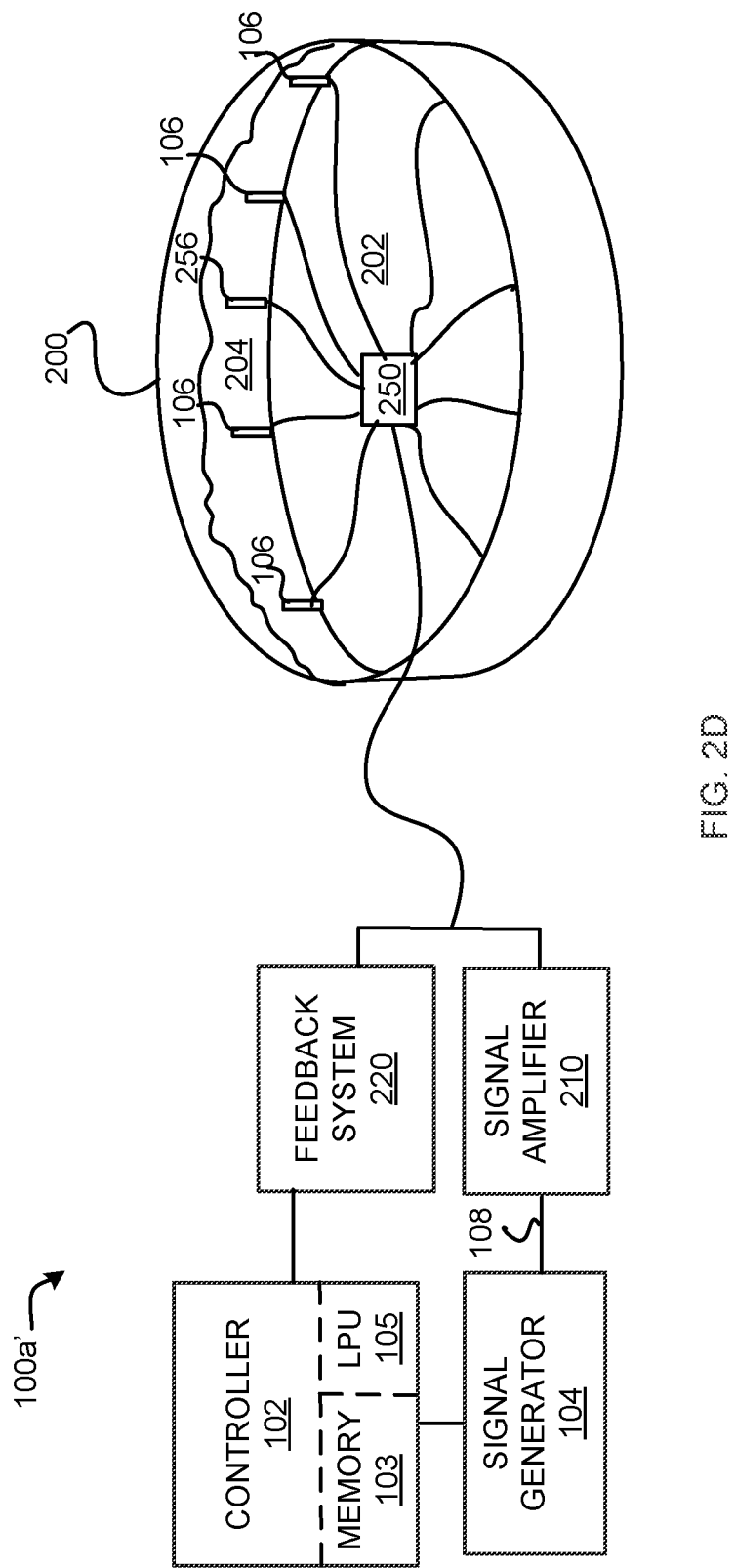

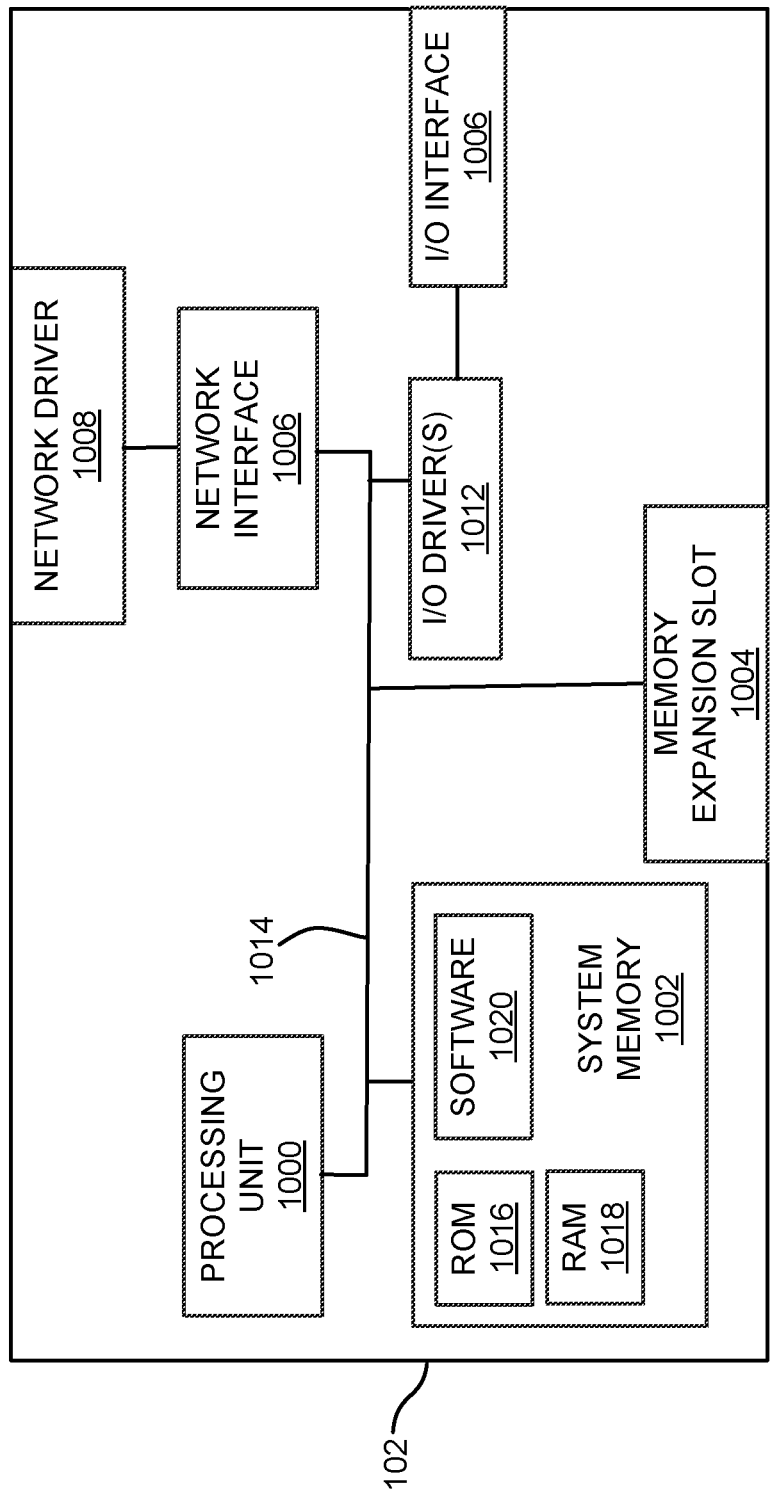

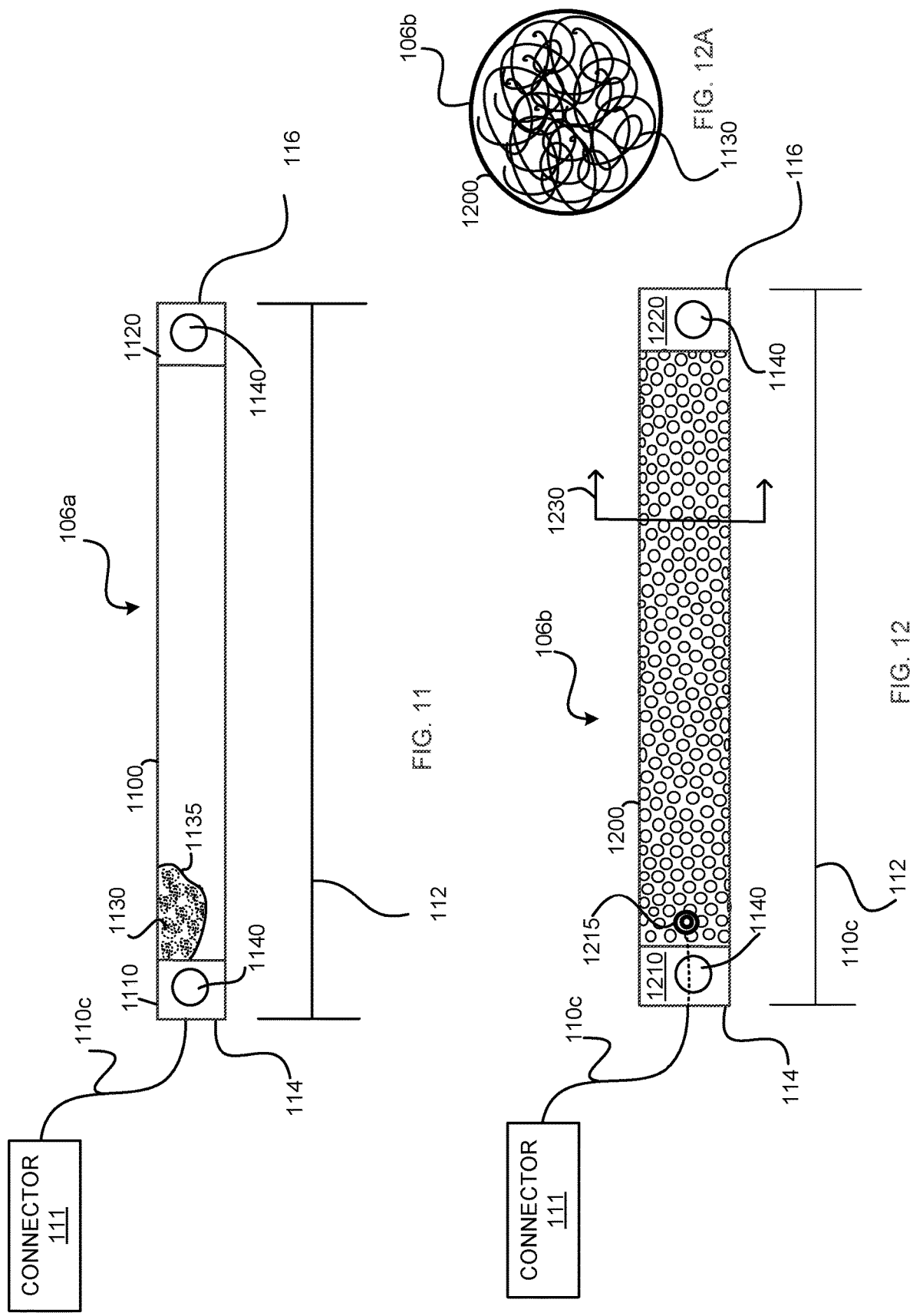

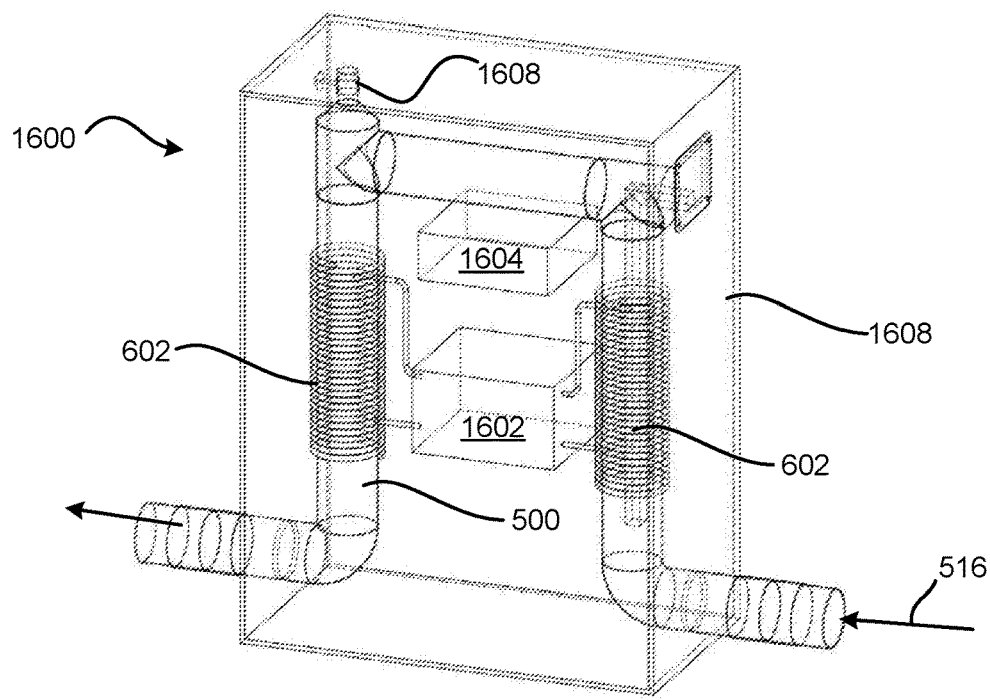
FIG. 16
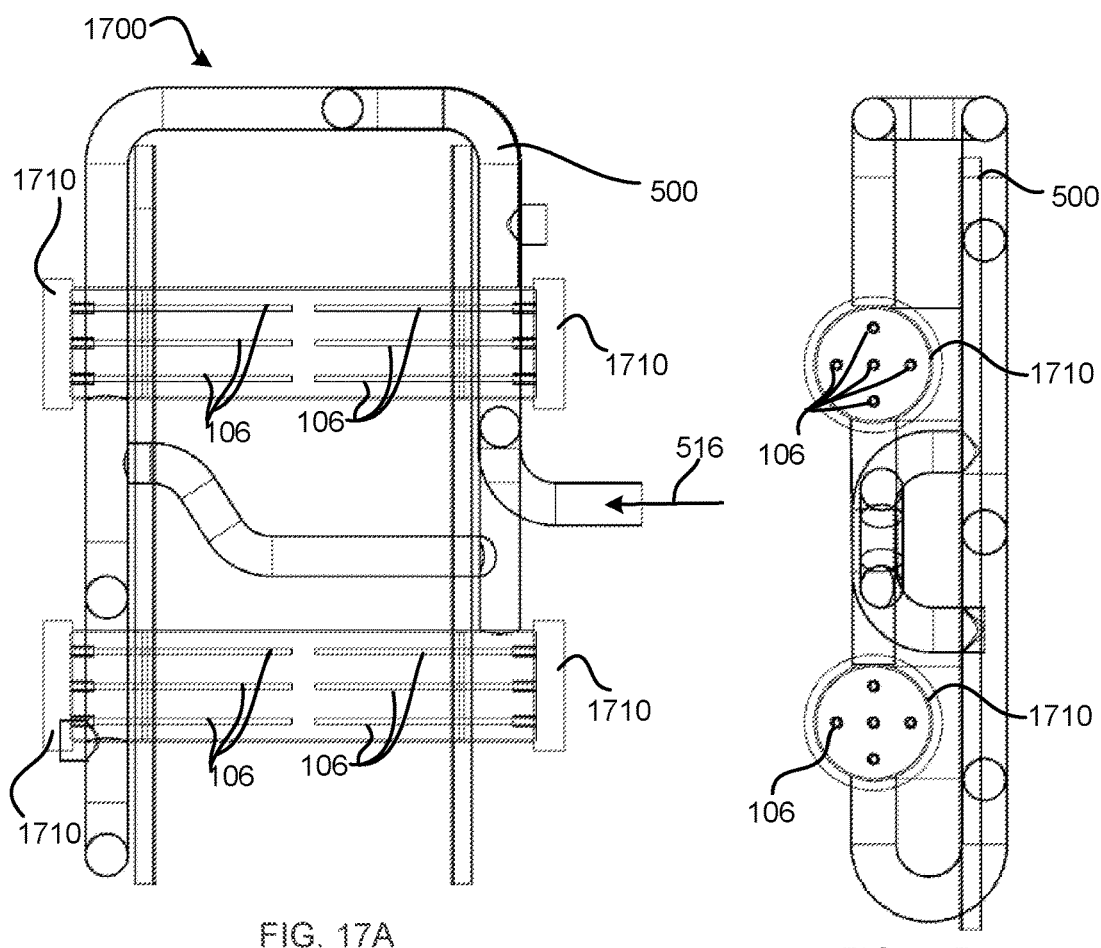
FIG. 17A
FIG. 17B

SYSTEMS AND METHODS FOR CLEANING AND STERILIZING FLUIDS AND ARTICLES USING ELECTROMAGNETIC WAVES

CROSS-REFERENCE TO RELATED APPLICATIONS

The present application claims benefit of Provisional Patent Application No. 62/659,010, filed on Apr. 17, 2018, entitled Systems and Methods for Cleaning and Sterilizing Fluids and Articles Using Electromagnetic Waves, that application being incorporated herein, by reference, in its entirety.

TECHNICAL FIELD

This description generally relates to cleaning and sanitizing fluids and articles, such as food items, and in particular to cleaning and sanitizing fluids and articles by using electromagnetic waves.

DESCRIPTION OF THE RELATED ART

Bacteria, viruses, and other pathogens present in water sources can have a significant detrimental impact to the health of a community. Although such pathogens may be removed by Pasteurization and other similar filtering processes, such methods may be expensive to implement. Moreover, such contaminated water may be harmful even if it is not consumed or drunk by members of the community. For example, Legionnaire's disease is transmitted by contaminated water sources, such as those used by water and cooling towers, when the water molecules become airborne.

U. S. Patent Application Publication No. 2008/0128283 to Van Rensburg (the "'283 publication") discloses a water purification apparatus including at least one emitter for emitting an electromagnetic wave having a specific frequency through water, with the specific frequency or harmonic component of the wave being similar to a resonant frequency of a particular impurity typically found in water in an attempt to destroy the impurity. The '283 publication does not disclose, among other things, emitting a range of frequencies in the hertz—very low kilohertz level to target a variety of impurities.

What is needed is a system that quickly targets a variety of impurities.

BRIEF SUMMARY

Systems and methods for treating water sources using RF waves to neutralize bacteria, viruses, and other pathogens provide an alternative for cleaning and sterilizing fluids. In some implementations, the RF waves are applied to the fluid via one or more emitters that are submerged within the fluid to be treated. The generated and applied RF wave should be of a sufficient amplitude and strength to propagate throughout the fluid and neutralize the bacteria, viruses, and other pathogens present in the fluid. In some implementations, an amplifier may be used to boost the strength of the RF wave to a desired level or amplitude. The frequency of the RF waves may be varied or swept across a frequency range to neutralize a wide variety of harmful bacteria, viruses, and other pathogens thereby removing such harmful organisms from the treated fluid. In some implementations, solid objects, including food items, may be sterilized by being immersed within fluid that is being treated with the RF waves. Such systems and method may be implemented within fluid reservoirs that hold various quantities of fluids. Such systems and method may be implemented with enclosed fluidic paths (e.g., pipes) that are used to transport fluid at varying flow rates between locations, such as from a fluid reservoir or well to a water tap.

In some implementations, the RF waves are applied to one or more wires that are wrapped or coiled around an exterior wall of a pipe. The voltage and current applied to such wires may oscillate, thereby inducing a magnetic field within the interior of the pipe. The magnetic field agitates the water molecules flowing through the pipe, thereby causing the water molecules to attract and attach to calcium and calcium carbonate deposits along the interior wall of the pipe. Such calcium and calcium carbonate materials build up as scale along the interior wall of the pipe. The water molecules may carry these particles away, thereby cleaning the interior wall of the pipe. In addition, such oscillations inhibit the growth of sludge and other biohazardous materials along the interior wall of the pipe.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

FIG. 1 is a schematic diagram of a radio frequency ("RF") cleaning and sterilization system, according to one particular embodiment of the invention;

FIG. 2A is an isometric view of an RF cleaning and sterilization system that has been incorporated into a fluid reservoir, in accordance with one particular embodiment of the invention;

FIG. 2B is an isometric dotted line view of the fluid reservoir of FIG. 2A with a solid item fully immersed in a fluid, in accordance with one particular embodiment of the invention;

FIGS. 2C and 2D are schematic diagrams illustrating of a further embodiment of a radio frequency ("RF") cleaning and sterilization system of the invention;

FIG. 10 is a block diagram of a control unit that may transmit signal used to vary the frequency of an RF signal transmitted by an RF signal generator, in accordance with one particular embodiment of the invention;

FIG. 11 is a side plan, partial cut-away view of an emitter in accordance with one embodiment of the invention;

FIG. 12 is a side plan view of an emitter in accordance with another embodiment of the invention;

FIG. 12A is a cross-sectional view of a portion of the emitter of FIG. 12 seen from cross-sectional line 1230;

FIG. 16 is a diagrammatic view of a household water filter in accordance with one embodiment of the invention;

FIG. 17A is a front plan view of an RF cleaning and sterilization system that can replace a UV filter in accordance with one embodiment of the invention; and FIG. 17B is a side plan cross-section of the device of FIG. 17A.

DETAILED DESCRIPTION OF THE INVENTION

Figure 2C:
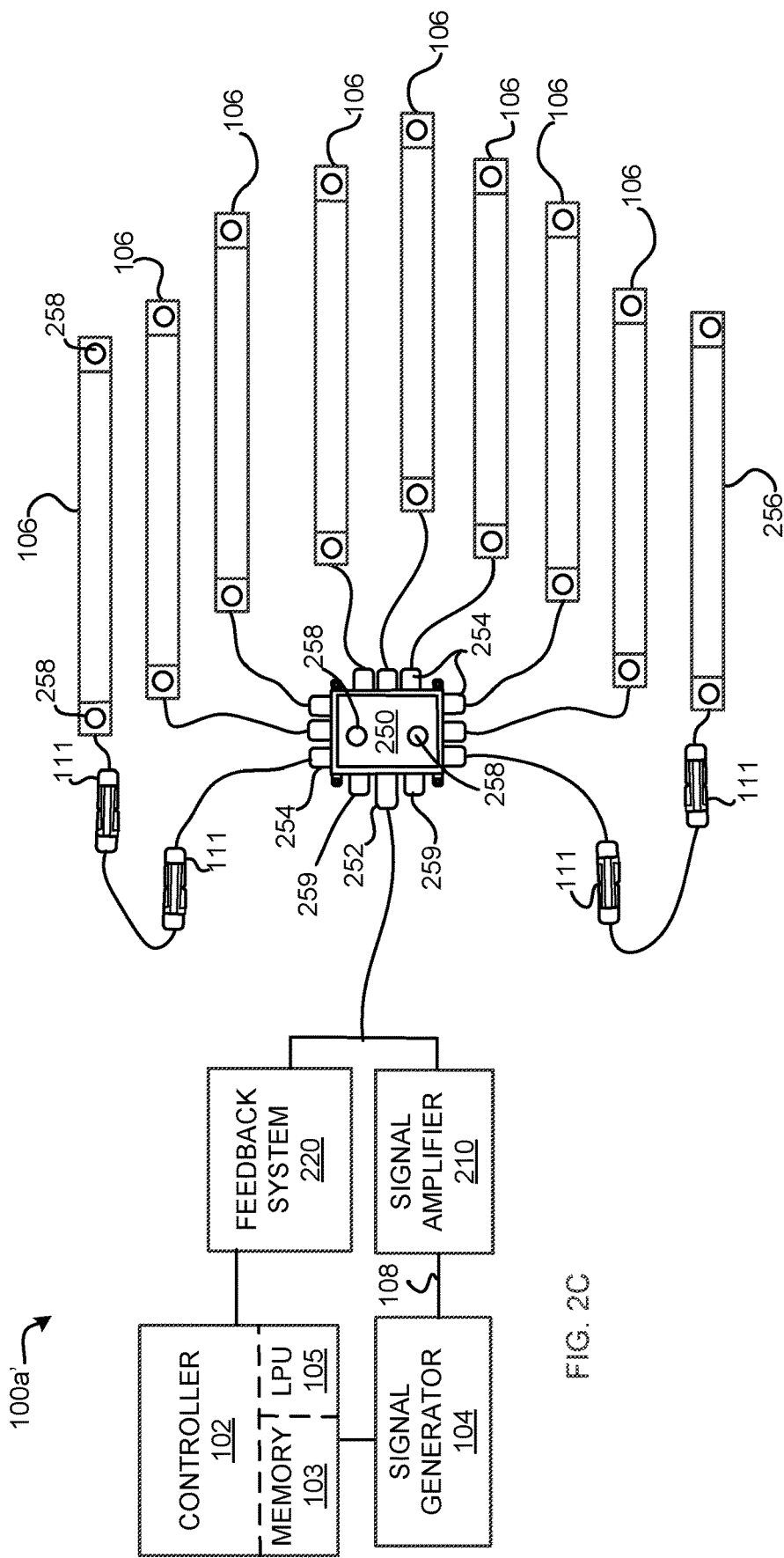

In the following description, certain specific details are set forth in order to provide a thorough understanding of various disclosed embodiments. However, one skilled in the art will recognize that embodiments may be practiced without one or more of these specific details, or with other methods, components, materials, etc. In other instances, certain structures associated with generating and transmitting electromagnetic waves have not been shown or described in detail to avoid unnecessarily obscuring descriptions of the embodiments. In other instances, certain structures associated with controlling the frequency of an electromagnetic signal generated by a variable frequency signal generator have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "a particular embodiment", "one embodiment" or "an embodiment" means that a particular feature, structure or characteristic described in connection with the embodiment is included in at least one embodiment. Thus, the appearances of the phrases "a particular embodiment", "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The headings and Abstract of the Disclosure provided herein are for convenience only and do not interpret the scope or meaning of the embodiments.

FIG. 1 shows a radio frequency ("RF") cleaning and sterilization system 100 that includes a controller 102, a signal generator 104, and an electrode or emitter 106. FIGS. 2A and 2B, show an exemplary embodiment of an RF cleaning and sterilization system 100a that further includes a signal amplifier 210 connected to a plurality of emitters 106. It should be understood that, optionally, the controller 102, signal generator 104 and signal amplifier 210 (if used) can be integrated into a single housing or control box 101 with additional elements of the system, such as a display and/or user interface, if desired.

Referring now to FIGS. 1-2B, the RF cleaning and sterilization systems 100, 100a may be used to eliminate bacteria, viruses, and other pathogen from various types of fluids by subjecting the fluids to a variable frequency RF waveform. Additionally, the RF cleaning and sterilization systems 100, 100a may be used to cleanse and sterilize items, including food items such as raw meat 212, by removing bacteria, viruses, and other pathogen from the surface of the items. Such items may be cleansed and sterilized by immersing the items in a fluid 206 that is subjected to a variable frequency RF waveform. Additionally, the RF cleaning and sterilization systems 100, 100a can be used to cleanse and sterilize fluids and fluid reservoirs, themselves, including, but not limited to, water tanks (such as tank 200), water towers, residential potable water sources, pools, hot tubs or spas, wells and other types of potable water sources and reservoirs of any size. Such a system can eliminate the use of chlorine in installations that traditionally use it to cleanse a fluid, such as the treatment of water on ships, in pools and in hot tubs. It should be noted that, in installations such as pools or hot tubs, emitters may be covered to avoid direct skin contact.

The controller 102 includes at least one processor or logic processing unit 105 connected to one or more processor-readable memories 103 storing one or more sets of processor-readable instructions for controlling the output of the signal generator 104. The memory 103 in the controller 102 may be supplemented with one or more slots configured to accept the insertion of one or more removable memory devices such as a secure digital (SD) card, a compact flash (CF) card, a universal serial bus (USB) memory "stick," or the like. The controller 102 may further include one or more logic processing units 105 that may execute the process-readable instructions stored in the memory 103. Such logic processing units 105 may include, any logic processing unit, such as, for example, one or more central processing units (CPUs), microprocessors, digital signal processors (DSPs), application-specific integrated circuits (ASICs), field programmable gate arrays (FPGAs), etc.

The controller 102 may be communicatively coupled to the signal generator 104 via the communications link 108. The communications link 108 may be a wired or wireless communications link (e.g., cellular radios, WI-FI radios, Bluetooth radios) for establishing communications over a network, for instance the Internet or a cellular network.

The signal generator 104 may be any type of component capable of generating and outputting an electromagnetic signal with a variable frequency. For example, a signal generator IC device can be used as the signal generator 104. In such an implementation, the frequency of the electromagnetic signal output by the signal generator 104 may be located with a frequency range that has a minimum frequency and a maximum frequency. For example, in some preferred embodiments, the signal generator 104 may generate an electromagnetic signal having a frequency within a frequency range of between 0 Hertz and 25 kilo-Hertz. In some implementations, the signal generator 104 may generator an electromagnetic signal having a frequency within the frequency range of between 0 Hertz and 30 kilo-Hertz.

In some embodiments, the signal generator 104 may perform a sweep of frequencies within the frequency range within a specified period of time, such as, for example, within 10 milliseconds or within 5 milliseconds. In such a situation, for example, the signal generator 104 may increase the frequency of the generated electromagnetic signal by an incremental value, such as, for example, 1 Hertz, 5 Hertz, 10 Hertz, or more, in sweeping between the minimum frequency and the maximum frequency. As such, in one exemplary embodiment, the signal generator 104 would perform a sweep of frequencies between 0 Hertz and 25 kilo-Hertz within 5 milliseconds or within 10 milliseconds. Additionally, if desired, the signals generated by the signal generator 104 may include waveforms of various shapes. For example, as desired, the signal generator 104 may generate electromagnetic waves in the form of sine-waves, square waves, saw-tooth waves, and other similar waveforms. Every bacteria has a specific resonance frequency that will destroy it. The frequency provided by the signal generator 104 can, therefore be programmed to target specific bacteria, or to create a range to destroy many at the same time. For example, the controller 102 can cause the frequency from the signal generator 104 to cycle through the frequency ranges, as desired.

The signal generator 104 may vary the amplitude, in terms of voltage and/or current, for example, of the electromagnetic waveform to be transmitted. In some implementations, the signal generator 104 may transmit an electromagnetic wave with an amplitude of 12 Volts, 20 Volts, 23 Volts, or more. In some implementations, the signal generator 104 may generate and transmit an electromagnetic wave that has a current of +/−65 milliamps. The output from the signal generator 104 is provided to one or more emitters 106, via the output connection(s) 110. The signal generator 104 may advantageously be placed close to, or proximate to, the emitter 106 to reduce the amount of electromagnetic waveform energy that is dissipated as a result of the resistive and inductive properties that may be inherent in the output connection(s) 110.

As discussed above in connection with FIGS. 2A and 2B, the signal generator 104 may include, or be coupled to, a signal amplifier 210, to increase the voltage and/or current of the electromagnetic wave that is transmitted to the emitter 106. In one particular embodiment, the amplifier can be used to adjust the power output from 0 to 110 Volts. This can be changed depending on the requirements of a particular application. Thus, the signal amplifier 210 enhances and increases the signal to ensure a more efficient and targeted kill. However, it should be noted herein, it is not the voltage that kills the bacteria in the present invention, but rather, the frequency emitted by the emitters 106 kill the bacteria when the emitters are powered by the voltage. Rather, every bacteria has a specific resonance frequency that will destroy it. The frequency can, therefore, be programmed to target specific bacteria or create a range to kill many at the same time.

The emitter 106 is an elongated structure having a length 112 that separates a first end 114 and a second end 116. In some embodiments, the length 112 of the emitter 106 may depend, at least in part, on the strength of the electromagnetic wave to be transmitted by the emitter 106. Thus, for example, an emitter 106 with a relatively longer length 112 may be used when a relatively stronger signal is needed, and a relatively shorter length 112 may be used for the emitter 106 when a relatively weaker signal is needed. In a preferred embodiment of the invention, the emitter length to sterilize and cleanse fluids by neutralizing and killing bacteria, viruses, and other pathogen is selected to be from 12 inches to and including 24 inches. In one particular embodiment of the invention, the width of the emitter 106 is about 50 mm. The cross-sectional area of the emitter 106 may be substantially circular (e.g., circular, elliptical, oval) in shape. The emitter 106 may be made from any suitable material that will transmit an electromagnetic wave 118 into the surrounding environment based on the electromagnetic wave received from the signal generator 104 via the output connection 110. The materials that comprise the emitter 106 may further resist or prevent corrosion when immersed in water or other fluids.

Referring now to FIGS. 1-2A and 11-12A, two particular embodiments of an emitter 106 that can be used as the emitters 106 in the systems 100, 100a, will be described. More particularly, emitter 106a has a cover made of a piece of PVC pipe 1100 enclosed at each end by a PVC endcap 1110, 1120. Additionally, a conductor 110c connected to the emitter 106a, through the cap 1110, provides a signal connection between the emitter 106 and the signal generator 104 and/or signal amplifier 210. In one particular embodiment, the cover 1100 between the two endcaps, 1110, 1120, is filled with stainless steel wool balls 1130, shown through the partial cut-away 1135 of the tube 1100.

Emitter 106b has a casing formed by a tube of perforated stainless steel 1200, enclosed at each end by a stainless steel endcap 1210, 1220. In the present embodiment, the conductor 110c passes through the endcap 1210 and is connected directly to the inside wall of the perforated stainless steel tube casing 1200 with a rivet 1215. In one particular embodiment, the cover 1200 between the two endcaps, 1210, 1220, is filled with stainless steel wool balls 1130. Water or another fluid in which the emitter 106b is immersed, can pass through the perforations in the steel casing, and also through the steel wool balls, while being treated. This results in less resistance and restrictions in water flow, and to a more efficient treatment.

According to one particular embodiment of the present invention, no other electrical components need be contained within the tubes 1100, 1200. Rather, the particular configuration of the emitters 106, 106a, 106b causes each emitter 106, 106a, 106b act as an "antenna" that emits certain desired frequencies (as described above) as a consequence of certain frequency signals being received on the conductor 110c from the signal generator 104. Further, whereas a conventional antenna typically emits frequencies at 90° angles to its surface, the steel wool 1130 of the present embodiment acts as a reflector in the emitter, providing more surface area in the container and causing the frequencies to be emitted at other angles relative to the surface of the emitter 106a, 106b. More particularly, each curve of the rolled-up, stainless steel balls in the emitter reflects the signal at 90° from the surface of the steel wool, thus providing a multi-array of signals in all direction in the media to be treated.

The designs of the present emitters 106, 106a, 106b are critical to the functioning of the claimed system. The length of each emitter is most important to its functioning, as the wavelength of the signal is dependent on the length of the "antenna" created. In particular, the length of the emitter is important for establishing resonant frequencies. In one particular embodiment, the length 112 of each emitter is a minimum of 12 inches.

Optionally, one or more connectors 111 can be provided between the emitter 106, 106a, 106b and the signal generator 104 and/or signal amplifier 210. Using the connectors 110, the conductor length 110c can be made to be short, and each of the lengths 110a and 110b can be customized for the placement locations of each emitter 106, 106a, 106b. Alternately, the connectors 111 can be omitted and a single conductor 110 can be used to connect each emitter 106, 106a, 106b to a signal generator 104 and/or signal amplifier 210.

Additionally, in one particular embodiment of the invention, strong magnets 1130, such as neodymium rare earth magnets, are attached to each end cap 1110, 1120, 1210, 1220, of the emitters 106, 106a, 106b, to simplify attachment of the emitter 106, 106a, 106b, to a metal surface within a metal tank or reservoir. This simplifies the placement of the emitters 106, 106a, 106b and eliminates any need for welding of the emitters 106, 106a, 106b to a particular location.

The electromagnetic waves emitted by the emitters 106, 106a, 106b neutralize microscopic organisms by agitating the organism at a "resonance frequency" that results in the membrane of the organism tearing apart. Various types of microscopic organism may have different "resonance frequencies." Accordingly, by emitting waveforms that sweep through a range of frequencies, the emitters 106, 106a, 106b may be used to neutralize multiple different types of organisms. Thus, for example, the bacteria that caused Legionnaire's disease may be neutralized by emitting a resonance frequency of between 3 kHz and 8 kHz. Other bacteria, viruses, and other pathogen may have resonance frequencies greater than 8 kHz (e.g., up to 25 kHz) or less than 2 kHz. In general three to five sweeps of the frequency range at a sufficient power level by the emitters 106 may be sufficient to neutralize a significant number of bacteria, viruses, and other pathogen, and in some situations, may result in all such organisms within a treated volume of fluid being neutralized. In addition, such technology may be used to sterilize and clean solid objects, such as food items, immersed in a fluid that is subject to the electromagnetic waves being emitted by the emitter 106.

It should be understood that other materials can be used to fabricate emitters 106 without departing from the scope or spirit of the present invention. For example, in one embodiment, the emitters 106 are made from graphite.

Referring now to FIG. 2A, there is illustrated an implementation of the RF cleaning and sterilizing system 100a in which a plurality of emitters 106 has been placed within a fluid reservoir 200. The fluid reservoir 200 has a bottom 202 and one or more side walls 204 that provide a water-tight container for holding a volume of fluid 206. The fluid reservoir 200 may or may not include a top, depending on the purpose of the reservoir 200. The fluid 206 may be any type of fluid, such as water or other cooling fluid used for cooling tanks, or potable water or other types of fluid for consumption by humans. In some embodiments, the fluid reservoir 200 may be, for example, a 20-ton, 30-ton, 60-ton, or greater, water holding tank such as those used to hold potable water on cruise ships. The invention is not meant to be limited only thereto, as other types of fluids and fluid reservoirs may be used in connection with the present invention. For example, the fluid reservoir 200 can be a reservoir for non-potable water, such as a swimming pool or hot tub. Although illustrated in FIGS. 2A and 2B as a cylindrical tank or reservoir, this is also not meant to be limiting, as other shapes of tank or reservoir may be used, including, but not limited to, those having a square or rectangular cross-section.

One or more emitters 106, such as emitters 106a and/or 106b, are arranged on or near the bottom 202 of the fluid reservoir 200. In embodiments in which multiple emitters 106 are used, the emitters 106 may be arranged symmetrically on or about the bottom 202 of the fluid reservoir 200. For example, in situations in which the fluid reservoir 200 is cylindrical with a central axis 208, the plurality of emitters 106 may be arranged on or near the bottom 202 of the fluid reservoir 200 and arranged in evenly spaced intervals around the central axis 208. The number of emitters 106 used within the fluid reservoir 200 may depend, at least in part, on the amount of fluid 206 held within the reservoir, the time that a volume of fluid 206 may spend in the fluid reservoir 200 (e.g., the turn-over rate for full fluid reservoirs 200), and the configuration of the fluid reservoir 200 (e.g., tanks with corners or crevices may require more emitters 106).

The emitters 106 (such as emitters 106a and 106b) may be electrically coupled to an amplifier 210 that is used to increase the amplitude of the signal being generated and output by the signal generator 104. In one particular embodiment, the amplifier 210 may output a signal having an amplitude of between 12 Volts and 20 Volts. In another particular embodiment, the amplifier 210 can adjust the power output from 0 to 110 Volts. To reduce the attenuation of the signal being transmitted from the amplifier 210 to the emitters 106, the amplifier 210 may be located at or near the fluid reservoir 200. However, if desired, one or both of the controller 102 and the signal generator 104, by contrast, may be located relatively further away from the fluid reservoir 200 in such an embodiment.

Referring now to FIG. 2B, a fluid reservoir 200 is shown with a solid item 212, such as a food product, fully immersed in the fluid 206. In one particular embodiment of the invention, the fluid is salt water, so as to better transfer the frequencies to the object.

In such an embodiment, the fluid reservoir 200 may be used to clean and/or sterilize the surface of solid items, such as food products, that have been immersed within the liquid held by the fluid reservoir 200. For example, in some embodiments, the fluid reservoir 200 may include a horizontal platform 214 that may be used to hold the solid item 212 completely submerged within the fluid 206 in the fluid reservoir 200 while the emitters 106 sweep across the desired frequency range for a set number of times (e.g., 3 to 5 or more sweeps for each solid item 212 to be sterilized or cleaned). In some embodiments, the fluid reservoir 200 may be included as a station along a conveyor system in which food items transported along a conveyor belt, or secured and suspended from an elevated track, may be immersed within the fluid 206 held in the fluid reservoir 200 while the emitters 106 sweep across a desired frequency range to neutralize bacteria, viruses, or other pathogen. In such an implementation, the fluid reservoir may hold 10-20 gallons of water or other fluid 206. Although illustrated as including continuous cables 110 between the emitters 106 and the amplifier 210, it should be understood that the cables 110 can alternately be made up of custom lengths of cable and connectors (111 of FIG. 1) assembled to make up a continuous signal conducting cable 110 to each emitter 106, if desired.

Referring now to FIGS. 2C and 2D, there is shown a further embodiment of an RF cleaning and sterilizing system 100a' that differs from system 100a of FIGS. 2A and 2B in that, among other things, instead of multiple lines 110 from amplifier 210 extending directly to each emitter 106 in the tank, a junction box 250 is provided. Junction box 250 includes a line-in connector 252, for receiving a voltage signal from the amplifier 210, and a plurality of emitter connectors 254. In one particular embodiment of the invention, junction box 250 has nine emitter connectors 254 that, in the present embodiment, are connected to eight emitters 106 and one reference or watchdog emitter 256. Additionally, in the exemplary embodiment illustrated, junction box 250 is provided with two additional connections 252, which may be used to connect sensors, such temperature sensors, RF coils and/or other devices to the junction box 250, and from the junction box 250, to the controller 102.

In one particular embodiment of the invention, the system 100a' has been provided with a feedback system 220 that gives a signal feedback received from the reference emitter 256 to the controller 102 to ensure that the emitters 106 are functioning as programmed. More particularly, a signal is provided by the reference emitter 256 that is forwarded to the controller 102, which is used to confirm that the system 100a' is on and functioning at a certain voltage and/or frequency. The reference emitter 256 may be the same type of emitter as emitters 106, described herein, or may be different. For example, in one particular embodiment of the invention, the reference emitter 256 does not include steel wool, therein. As such, the reference emitter 256 can be made as a hollow steel tube without the steel wool, or even a steel rod or pipe.

Each emitter 106, 256 of the system 100a' can be connected to the junction box by a single cable cut to size, or by a plurality of cable segments connected by together by one or more connectors 111, to form a single, signal connector to the emitter 106 and/or reference emitter 256, as desired. Additionally, in one particular embodiment of the invention, each emitter 106 and reference emitter 256 have been fitted with two covered, neodymium magnets 258 (one at each end), to help ensure that the emitters 106, 256 are attached securely to the metal walls of the tank or reservoir 200 without drilling, welding or requiring extra installation parts. In this embodiment, junction box 250 additionally includes one or more magnets 258.

In use, the junction box 250 is secured to a floor 202 or wall 204 of a reservoir 200 by the magnets 258. A single cable bundle comes in to the junction box 250 from the signal amplifier 210. Each emitter 106 and the reference emitter 256 are secured to a wall 204 or floor 202 of the reservoir in a spaced relationship using the magnets 258, and is also connected to the junction box 250 by its own signal cable(s) and/or connectors 111. In one particular preferred embodiment of the invention, the emitters 106 and reference emitter 256 are secured to a wall 204 of the reservoir 200 at about a mid-point, in height. In another embodiment of the invention, the emitters 106 are secured to the wall 204 of the reservoir between 4-6 feet above the bottom of the reservoir 200. If desired, emitters 106 can be secured to the walls 204 of the reservoir at different heights from one another. Additionally if desired, one or more emitters 106 can be mounted to the floor 202 of the reservoir 200.

In one particular embodiment, the system 100a' can have up to 16 emitters per controller 102. However, this is not meant to be limit the invention to only 16 emitters. There is no limit to the number of emitters that can be used, as it can vary (more than 16 or less than 16) depending on the size of the receptacle to be treated and the type of bacteria that is present. The number of emitters can, therefore, also be expanded to be able to treat much bigger tank volumes or lessened to treat smaller volumes. A small system with a 1000 W signal amplifier can sanitize a water tank containing 600 tons of water.

Figure 3:
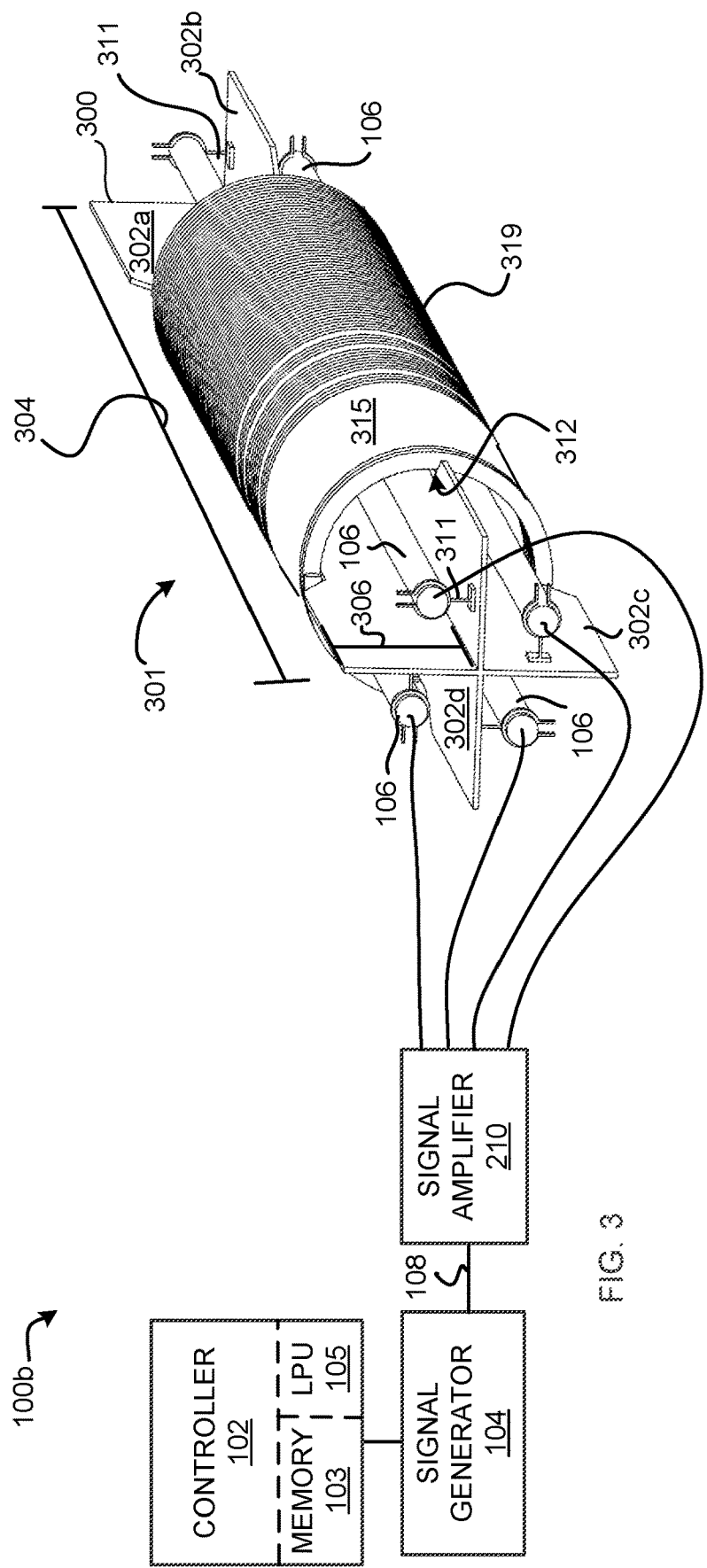
FIG. 3 is an isometric view of an RF cleaning and sterilization system in which a plurality of emitters have been mounted onto an emitter holder, in accordance with one particular embodiment of the invention.
Figure 4:
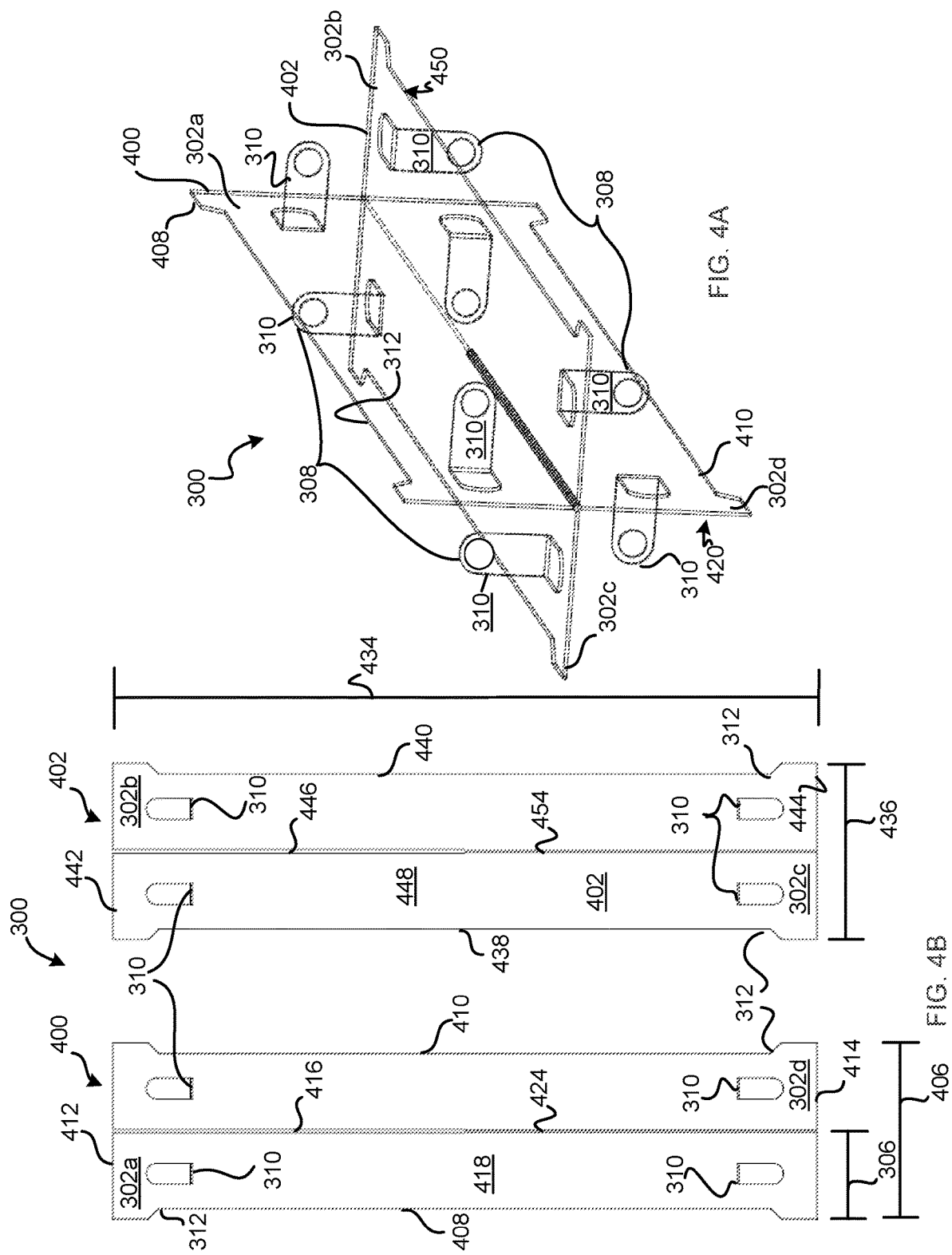
FIG. 4A is an isometric view of the components of an emitter holder according to one particular embodiment of the present invention.
FIG. 4B is a top plan view of the individual components making up the emitter holder of FIG. 4A, separated from one another.

Referring now to FIGS. 3-4B, there will be described an embodiment of an RF cleaning and sterilizing system 100b in which a plurality of emitters 106 are mounted within an emitter holder 300. The emitter holder 300 may be comprised of four extensions, a first extension 302a, a second extension 302b, a third extension 302c, and a fourth extension 302d (collectively, "extensions 302"), in which the first extension 302a opposes the third extension 302c, and the second extension 302b opposes the fourth extension 302d. Each of the extensions 302 may have a length 304 and width 306. In some embodiments, the widths 306 for each of the extensions 302 may be equal. In some embodiments, the widths of each of the extensions 302 may vary.

Each of the extensions 302 may include an emitter bracket 308, each of which may be used to securely hold one emitter 106. Each emitter bracket 308 may include two tabs 310 or retention spring clips 311 that oppose each other and are spaced relatively apart from each based upon the length 112 of the emitter 106 to be held. As such, each pair of corresponding tabs 310 or clips 311 may extend outwardly from one of the extensions 302 of the emitter holder 300. In addition, each extension 302 may include a recessed portion 312 that may be used to wrap a covering 315 around the emitter holder 300. Such a covering 315 may be used, for example, to shield the waveforms emitted by the emitters 106 from interfering and potentially destructive waveforms that might reduce the effectiveness of the waveforms being emitted by the emitters 106. In some embodiments, such a covering may include a Faraday shield that may be used to isolate the waveforms being emitted by the emitters 106.

FIGS. 4A and 4B, in particular, show the emitter assembly 300, including a first emitter plate 400 and a second emitter plate 402, which together are combined into the emitter holder 300 shown in FIG. 3. The first emitter plate 400 has a length 404 and width 406. The first emitter plate 400 has a first edge 408 and a second edge 410 separated by the width 406, and a third edge 412 and a fourth edge 414 separated by the length 404. The first edge 408 and the second edge 410 may include the recessed portion 312. The third edge 412 may include a slot 416 that begins at a midpoint of the third edge 412 and extends along a longitudinal centerline for approximately half the length 304 of the first emitter plate 400.

The first emitter plate 400 may include a first face 418 and a second face 420 separated by a thickness. The first emitter plate 400 may include two sets of emitter brackets 308. The first set of emitter brackets 308a may be located proximate the second edge 410 and may extend perpendicularly outward from the first face 418. The two tabs 310 that comprise the first set of emitter brackets 308 may be sufficiently spaced apart from each other towards the third edge 412 and the fourth edge 414 of the first emitter plate 400 to securely hold an emitter 106 (FIG. 3) extended outward from the first face 418 of the first emitter plate 400. The second set of emitter brackets 308 may be located proximate the first edge 408 and may extend perpendicularly outward from the second face 420. The two tabs 310 that comprise the second set of emitter brackets 308 may be sufficiently spaced apart from each other towards the third edge 412 and the forth edge 414 of the first emitter plate 400 to securely hold an emitter 106 (FIG. 3) outward from the reverse face 420 (opposite to face 418) of the first emitter plate 400.

The second emitter plate 402 has a length 434 and width 436. In some embodiments, the length 434 and/or width 436 of the second emitter plate 402 may be equal to the corresponding length 404 and/or width 406 of the first emitter plate 400. In some embodiments one or both of the length 434 and width 436 of the second emitter plate 402 may be different from the corresponding length 404 and width 406 of the first emitter plate 400. The second emitter plate 402 has a first edge 438 and a second edge 440 separated by the width 436, and a third edge 442 and a fourth edge 444 separated by the length 434. The first edge 438 and the second edge 440 may include the recessed portion 312. The fourth edge 444 may include a slot 446 that begins at a midpoint of the fourth edge 442 and extends along a longitudinal centerline for approximately half the length 434 of the second emitter plate 402.

The second emitter plate 402 may include a first face 448 and a second face 450, opposite the first face 448 and separated by a thickness. The second emitter plate 402 may include two sets of emitter brackets 308. The first set of emitter brackets 308 may be located proximate the second edge 440 and may extend perpendicularly outward from the first face 448. The two tabs 310 that comprise the first set of emitter brackets 308 may be sufficiently spaced apart from each other towards the third edge 442 and the fourth edge 444 of the second emitter plate 402 to securely hold an emitter 106 (FIG. 3) extended outward from the first face 448 of the first emitter plate 402. The second set of emitter brackets 308 may be located proximate the first edge 438 and may extend perpendicularly outward from the second face 450 of the second emitter plate 402. The two tabs 310 that comprise the second set of emitter brackets 308d may be sufficiently spaced apart from each other towards the third edge 442 and the forth edge 444 of the second emitter plate 402 to securely hold an emitter 106 (FIG. 3) outward from the second face 450 of the second emitter plate 402.

In a preferred embodiment, the slot 416 on the first emitter plate 400 aligns with, and is physically engaged with, the corresponding slot 446 on the second emitter plate 402. As such, the slot 416 on the first emitter plate 400 may have a width that is greater than the thickness of the second emitter plate 402 such that the slot 416 on the first emitter plate 400 may extend over a solid portion 454 of the second emitter plate 402 from the end of the slot 446 to the third edge 442 of the second emitter plate 402. In such embodiments, the slot 446 on the second emitter plate 402 may have a width that is greater than the thickness of the first emitter plate 400, such that the slot 446 on the second emitter plate 402 may extend over a solid portion 424 of the first emitter plate 400 from the end of the slot 416 towards the fourth edge 414 of the first emitter plate 400. When the first emitter plate 400 and the second emitter plate 402 are so coupled, the first face 418 and the second face 420 of the first emitter plate 400 may each be perpendicular to the first face 448 and the second face 450 of the second emitter plate 402, as illustrated in FIG. 4A. As such, the first emitter plate 400 may couple to the second emitter plate 402 along the longitudinal centerline of the first emitter plate 400 and the longitudinal centerline of the second emitter plate 402.

Figure 5:
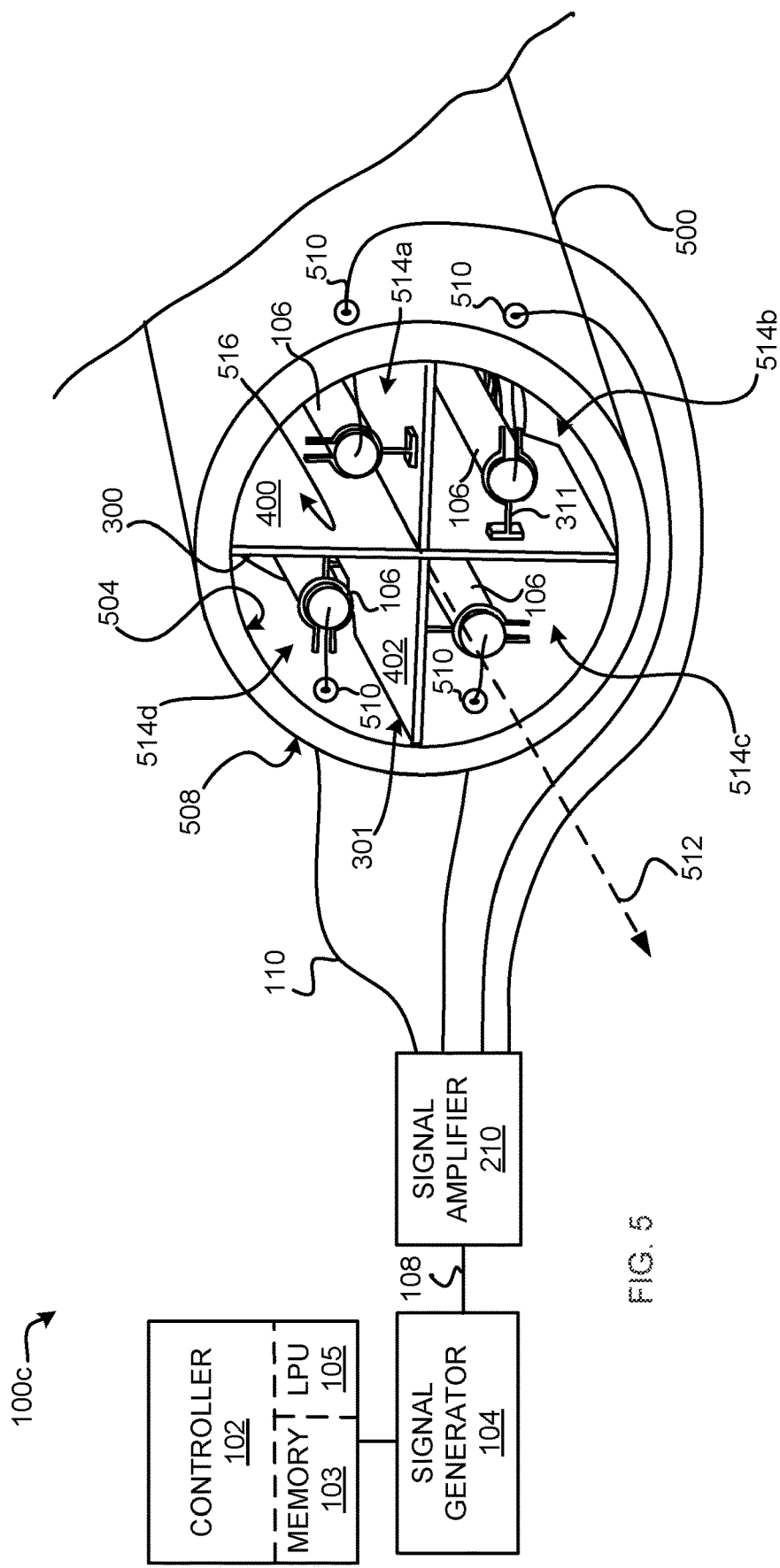
FIG. 5 is an isometric view of the emitter holder from FIG. 3 loaded into a pipe that forms an enclosed fluidic path, in accordance with one particular embodiment of the invention.

FIG. 5 shows another embodiment of an RF cleaning and sterilizing system 100c in which the emitter holder 300 is mounted with four emitters 106 and the entire assembly 301 (see FIG. 3) is installed within an interior portion of a pipe 500. Although clamps 311 are illustrated in FIG. 5, it should be understood that this is not meant to be limiting, as tabs, such as tabs 310 of FIG. 4A, may be used instead. The pipe 500 has an interior diameter defined by the diameter of an interior wall 504 of the pipe 500, and an exterior diameter defined by the exterior wall 508 of the pipe 500. Each of the interior diameter and the exterior diameter continue along a central axis 512 of the pipe 500. Referring now to FIGS. 4A-5, the interior diameter of the pipe 500 may be slightly larger than the widths 406, 436 of the emitter plates 400, 402, respectively. In some embodiments, the interior wall 504 may be sized and shaped to securely hold the emitter holder 300 in place via frictional forces between the respective edges of the first emitter plate 400 and the second emitter plate 402 that come into contact with the interior wall 504. The output connections 110 may extend from the signal amplifier 210 to the respective emitters 106 via one or more watertight apertures 510 that extend from the exterior wall 508 to the interior wall 504 of the pipe 500. The watertight apertures 510 may include a flexible, expandable, water-tight substance, such as rubber, a polymer, or like substances that will come into contact and make a watertight seal with the edges of the apertures 510.

The emitter holder 300 extends each of the emitters 106 into an enclosed fluidic path 516 formed by the interior wall 504 of the pipe 500, such that, in the present embodiment, the lengths of the emitters 106 extend parallel to the central axis 512 of the pipe 500. In some embodiments, the emitter holder 300 may arrange the plurality of emitters 106 symmetrically around the central axis 512 of the pipe 500 within the enclosed fluidic path 516. Thus, as shown in FIG. 5, the emitter holder 300 holding four emitters 106 may divide a cross sectional area of the pipe 500 into four quadrants 514a-514d, with each one of the emitter 106 occupying a separate one of the quadrants 514a-514d. An emitter holder with more or fewer emitters may similarly arrange the emitter symmetrically around the central axis 512 within the enclosed fluidic path 516. Although the RF cleaning and sterilization system 100c is shown with an amplifier 210 generating the electromagnetic waves for the output connections 110, such electromagnetic signals may be generated with sufficient power by the signal generator 104 to not need the amplifier 210.

Additionally, it is possible that the inner diameter of the pipe 500 will be much greater than the width of the emitter plates 400, 402. In such a case, extensions may be affixed to the plates 400, 402, or a holder or adapter may be used that is sized to support the emitter holder 300 inside the tube 500, centered about the central axis 512, while permitting fluid flow 516 about the holder 300.

The length (112 of FIG. 1) of each emitter 106 in the RF cleaning and sterilizing system 100c may depend, at least in part on the flow rate of the fluid through the portion of the pipe 500 that surrounds the emitter holder, as well as the time period for the signal generator 104 to sweep across a desired frequency range. For example, in embodiments in which the signal generator 104 takes 5 milliseconds to sweep across a desired frequency range, and a volume of water is to be subject to at least three sweeps, then the desired lengths of the emitters 106 may be 15 milliseconds times the flow rate of the fluid. Thus, in the preceding example, when the flow rate of the fluid equals 1 inch per millisecond, the desired length of the emitters 106 may be equal to at least 15 inches.

Additionally, referring now to FIGS. 3 and 5, if desired, the emitter assembly 301, including the holder 300, the emitters 106 and the covering 315, can have an RF coil or wire 319 wrapped around the outer wall of the covering 315. An electric signal in the form of a square wave, or other waveform, may be generated by the signal generator 104 and applied to the wire 319 that is coiled around the assembly 301. In one particular embodiment, the electromagnetic wave generated and transmitted by the signal generator is about +/−65 milliamps and/or about +/−5 Volts. When the electromagnetic square wave is applied to the wire coil 319, an oscillating magnetic field is induced around the assembly 301. If the assembly 301 is located within the interior of a portion of a pipe 500, as illustrated in FIG. 5, the oscillating magnetic wave agitates the water molecules flowing through the enclosed fluidic path 516 of the pipe 500. The water molecules at this point are loosely bound by mineral ions, such as calcium or calcium carbonate molecules. By agitating the water molecules at least some of the mineral ions become detached from the water molecules. The mineral ions thereby form nucleation sites for adjacent mineral ions to join. The continuous joining of mineral ions results in a relatively large water-insoluble crystal formed of mineral ions in which the charge locations reside within the interior of the crystal. As a result, the agitation of the water molecules results in an increased number of free water molecules that attract and attach to the calcium molecules present in the scale that has built up along the interior wall 504 of the pipe 500. The water molecules thereby breakdown the scale buildup along the interior wall 504 of the pipe 100. In addition, the excitation of the pipe 500 may inhibit the growth of the biohazardous film along the interior wall 504 of the pipe 500, thereby controlling the spread of bacteria and viruses. The above-described system works in all pipes, including ferrous pipes.

Figure 6:
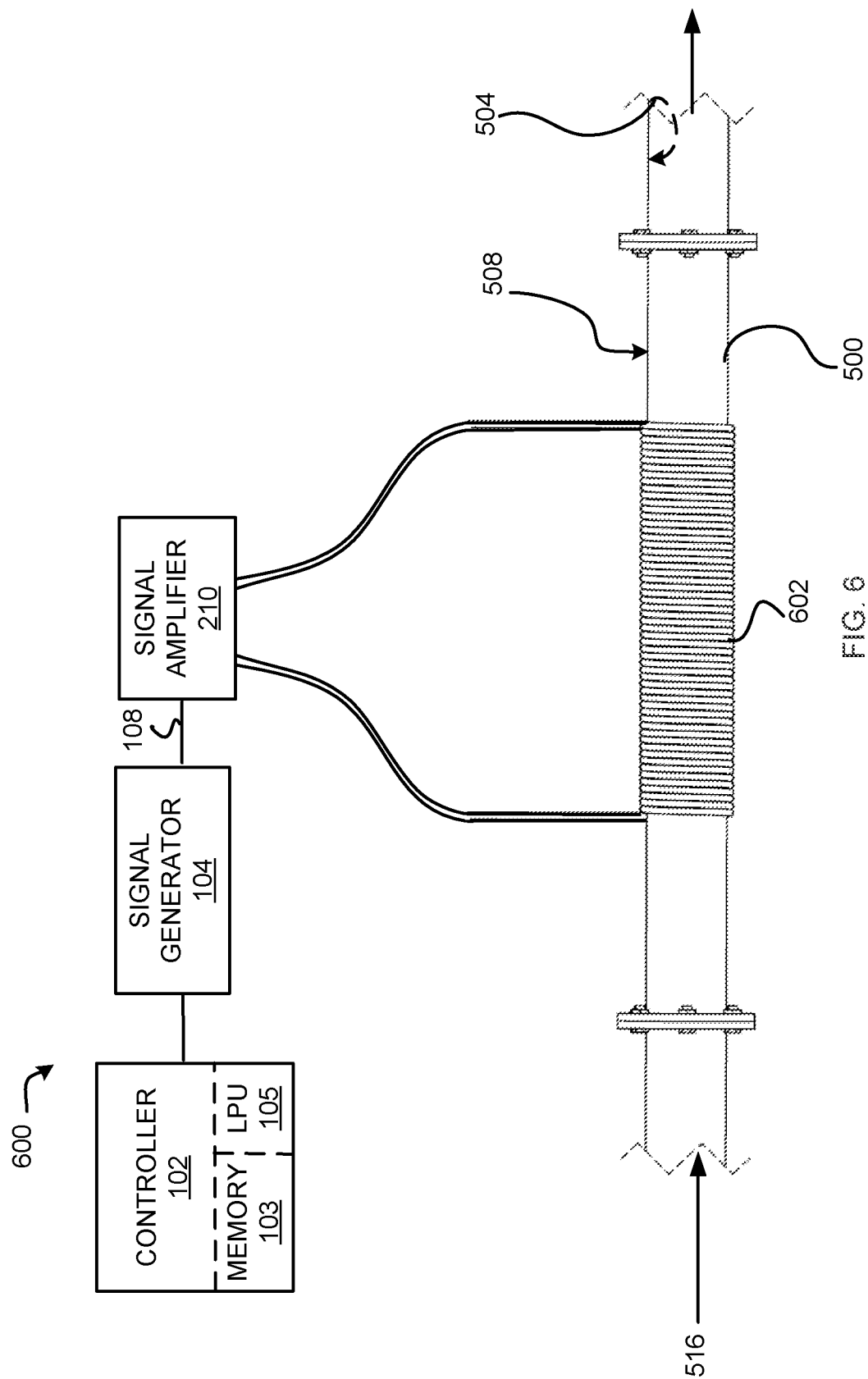
FIG. 6 is an isometric view of an RF cleaning and sterilization system in which a wire is wrapped around an exterior portion of a pipe, in accordance with one particular embodiment of the invention.

As an alternative to locating a coil inside the pipe for treating scale buildup and biofilm, a coil can also be outfitted around the outside of a non-ferrous pipe for treatment of biofilm and scale. Referring now to FIG. 6, there is shown one particular embodiment of a coiled version 600 of an RF cleaning and sterilization system in which a wire 602 is wrapped around the exterior wall 508 of a portion of the pipe 500. In some embodiments, the pipe 500 may be composed of PVC material or of copper. The interior diameter of the pipe 500 may be about 1 inch or less. An electric signal in the form of a square wave may be generated by the signal generator 104 and applied to the wire 602 that is coiled around the exterior wall 508 of the pipe 500. The electromagnetic wave generated and transmitted by the signal generator may be about +/−65 milliamps and/or about +/−5 Volts.

As discussed above, the buildup along the interior wall 504 may include mineral deposits, such as calcium carbonate, that form scales along the interior wall 504, as well as biohazardous film that may attach to or become trapped proximate the interior wall 504. When the electromagnetic square wave is applied to the wire 602 coiled around the exterior wall 508 of the pipe 500, an oscillating magnetic field is induced within the interior of the portion of the pipe 500 surrounded by the wire 602. The oscillating magnetic wave agitates the water molecules flowing through the enclosed fluidic path 516 formed by the interior wall 504 of the pipe 500. Through this agitation, the water molecules breakdown the scale buildup along the interior wall 504 and may inhibit the growth of the biohazardous film along the interior wall 504 of the pipe 500, thereby controlling the spread of bacteria and viruses. The system 600 can additionally include a temperature sensor connected to the controller 102, to turn off the signal generator 104 if the temperature in the coils 602 exceed a threshold.

Figure 7A:
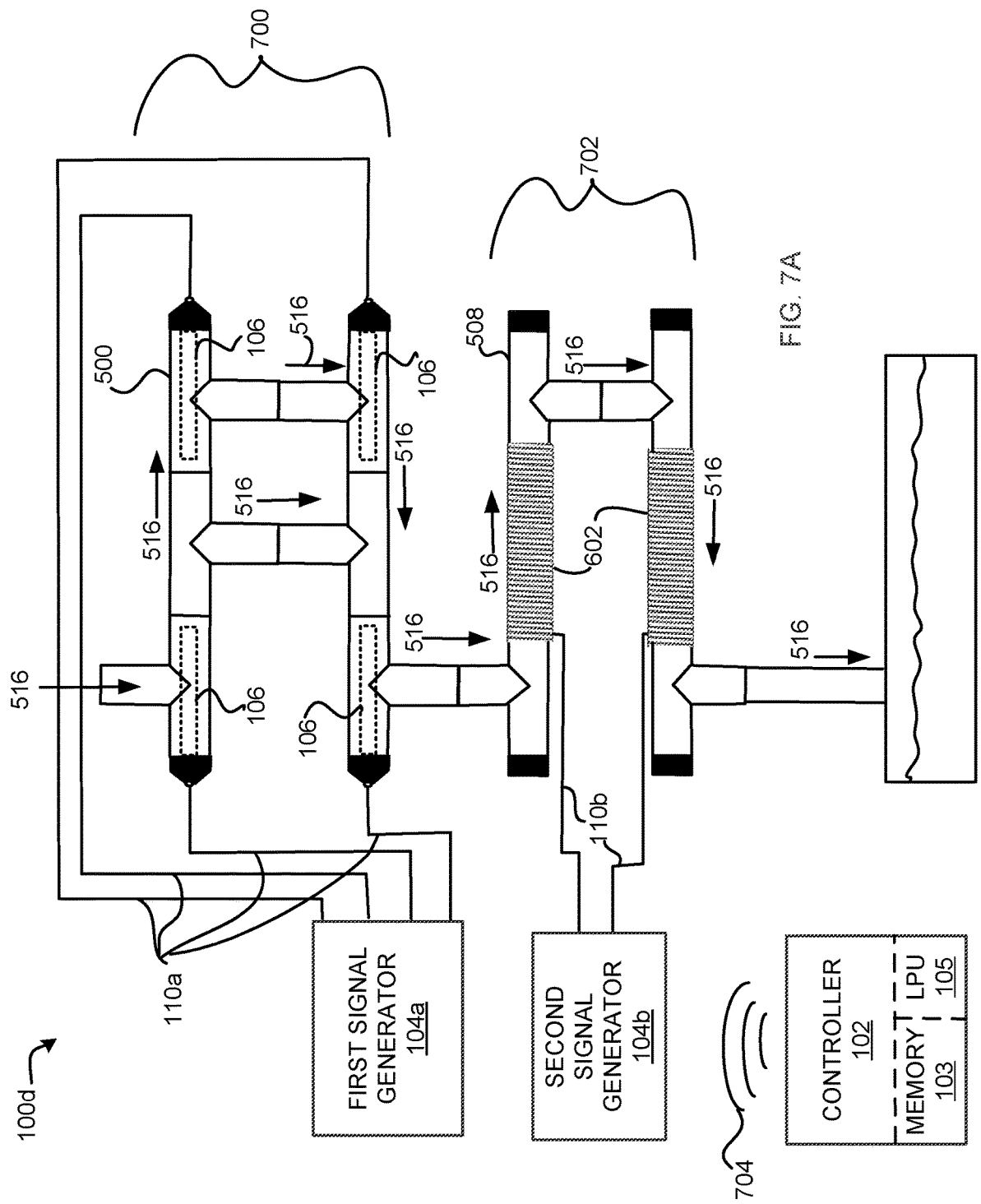
FIG. 7A is an isometric view of an RF cleaning and sterilization system in which a plurality of emitters have been inserted into a first portion of a pipe that forms an enclosed fluidic path, and a plurality of wires have been wrapped around exterior walls in a second portion of the pipe, in accordance with one particular embodiment of the invention.

FIG. 7A shows one embodiment of the RF cleaning and sterilization system 100*d* in which a first portion 700 of the pipe 500 surrounds multiple emitters 106 and a second portion 702 of the pipe 500 is wrapped in one or more wires 602. In such an embodiment, the enclosed fluidic path 516 proceeds past at least two emitters 106 inserted within the first portion 700 of the pipe 500.

In one particular embodiment of the invention, the system 100*d* includes at least two signal generators 104*a*, 104*b*. In such an embodiment, emitters 106 are electrically coupled to a first signal generator 104*a* via lines 110*a*, which may sweep the frequency of an output wave form across a frequency range from 0 Hertz to 25,000 Hertz within a span of between 5 milliseconds to 10 milliseconds. Such frequency sweeps may result in the neutralization of many, and potentially all, bacteria and viruses contained in the fluid.

After the first portion 700, the enclosed fluidic path 516 continues to the second portion 702 of the RF cleaning and sterilization system 100*d*, in which at least two sets of wires 602 are wrapped or coiled around the exterior walls 508 of the pipe 500. Each of these two wires 602 may be electrically coupled to a second signal generator, which may generate a square wave signal with a frequency that is swept from between 2,000 Hertz and 24,000 Hertz, thereby increasing the number of free water molecules present in the fluid being transported along the enclosed fluidic path 516. As such, the free water molecules may thereby attach to calcium and calcium carbonate build up that may create scale in later portions of the pipe 500.

The controller 102 may communicate with each of the signal generators 104*a* and 104*b* via a wireless connection 704. Such communications between the controller 102 and the signal generators 104*a* and 104*b* may be via a wired and/or wireless network architecture, for instance wired and wireless enterprise-wide computer networks, intranets, extranets, telecommunications networks, cellular networks, paging networks, and other mobile networks. For example, a control box (101 of FIG. 2A) containing the controller 102, signal generators 104*a* and 104*b* and other parts can also be used, if desired. Among other things, the system 100*d* can be used in connection with the sterilization and treatment of sewage.

Figure 7B:
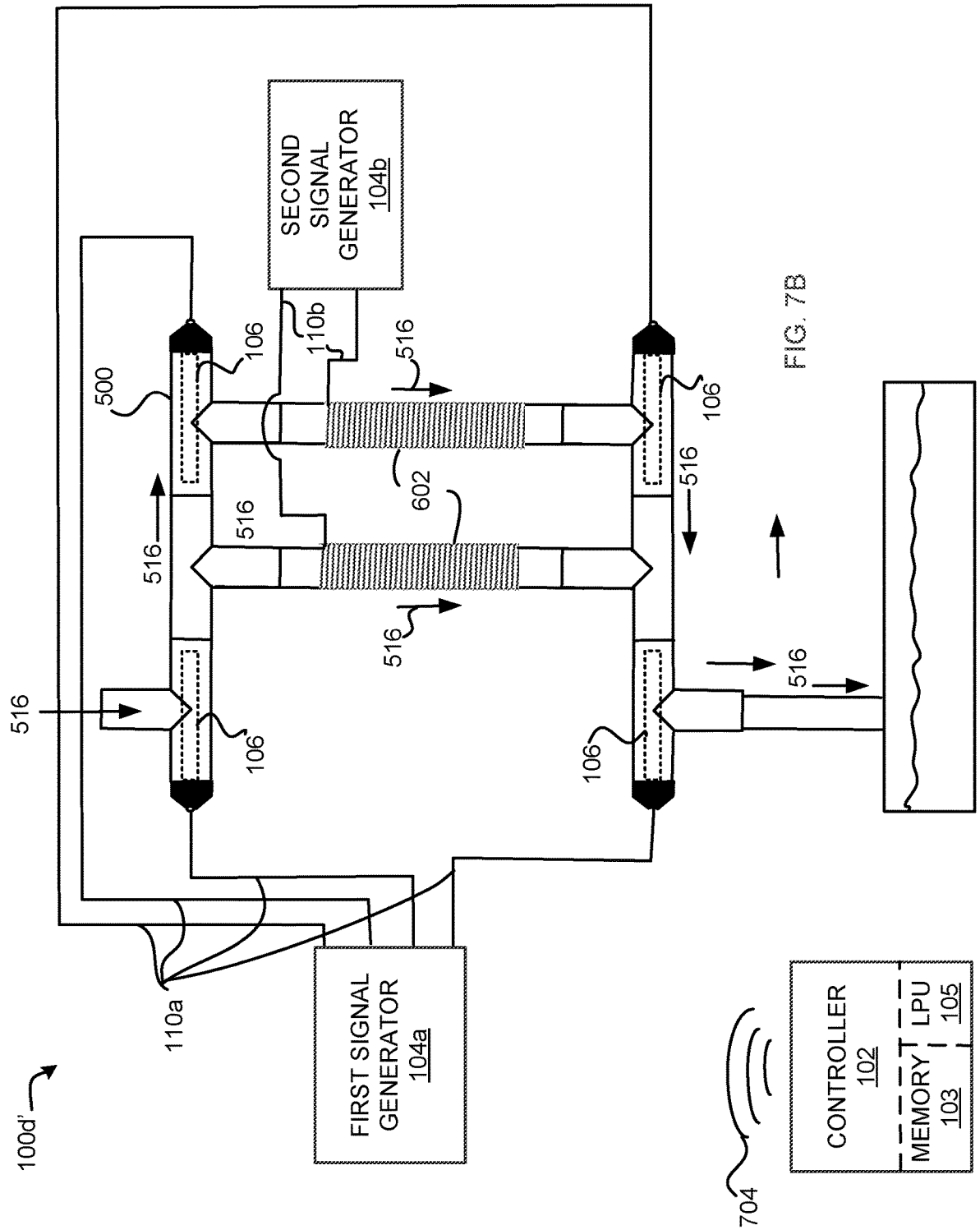
FIG. 7B is an isometric view of another embodiment of an RF cleaning and sterilization system including a plurality of emitters inserted into an enclosed fluidic path, and a plurality of wires wrapped around exterior walls of pipe through which the fluidic path extends.
Figure 8:
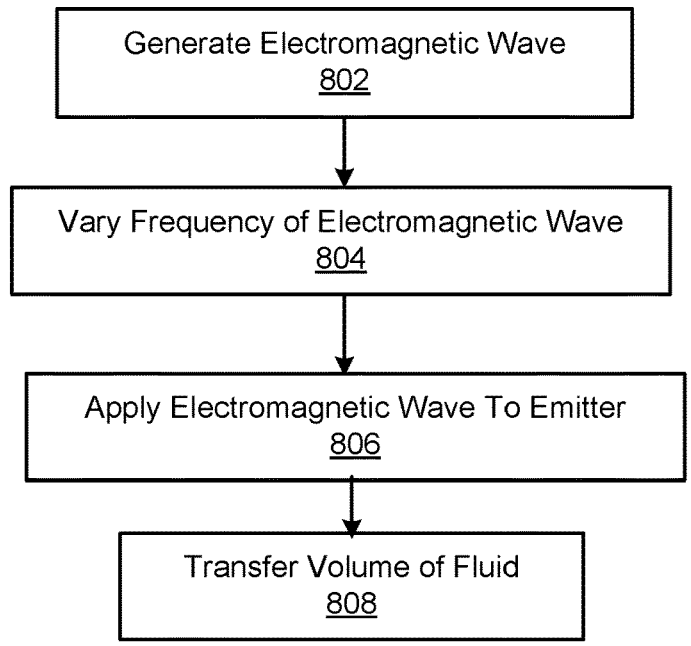
FIG. 8 is a flow diagram of a method for generating an RF signal with variable frequency that is transmitted from an emitter that is surrounded by an enclosed fluidic path, in accordance with one particular embodiment of the invention.
Figure 9:
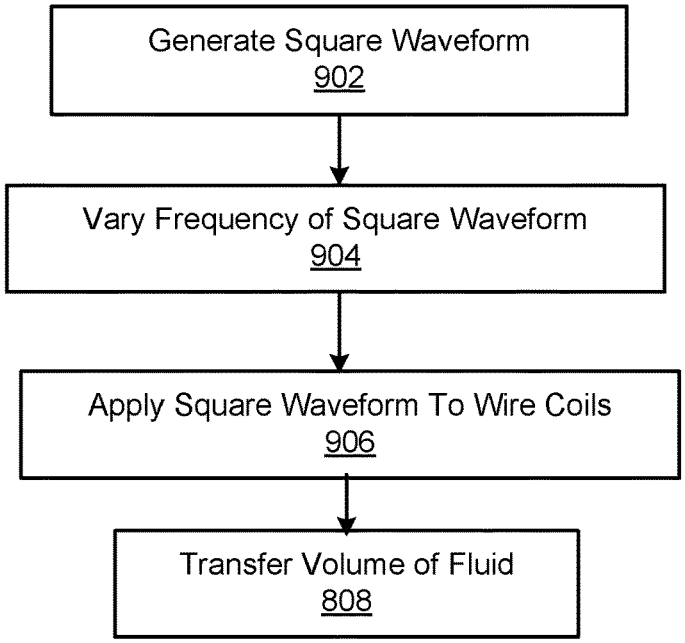
FIG. 9 is a flow diagram of a method for generating an RF signal with variable frequency that is transmitted to a wire that is wrapped around an exterior wall of a pipe, in accordance with one particular embodiment of the invention.

FIG. 7B shows an alternate configuration of an RF cleaning and sterilization system, such as the system 100*d* of FIG. 7A. In the system 100*d'* of FIG. 7B, the system is not divided into an emitter section 700 and a coil section 702. Rather, in the system 100*d'*, the coils 602 are interposed between two sections including emitters 106. Otherwise, the system 100*d'* operates in the same fashion as described in connection with the system 100*d* of FIG. 7A. The system 100*d'* can additionally be used for cleansing fluids, including sewage, and can be used in place of UV lighting systems that perform the same or a similar function.

Figure 13A:
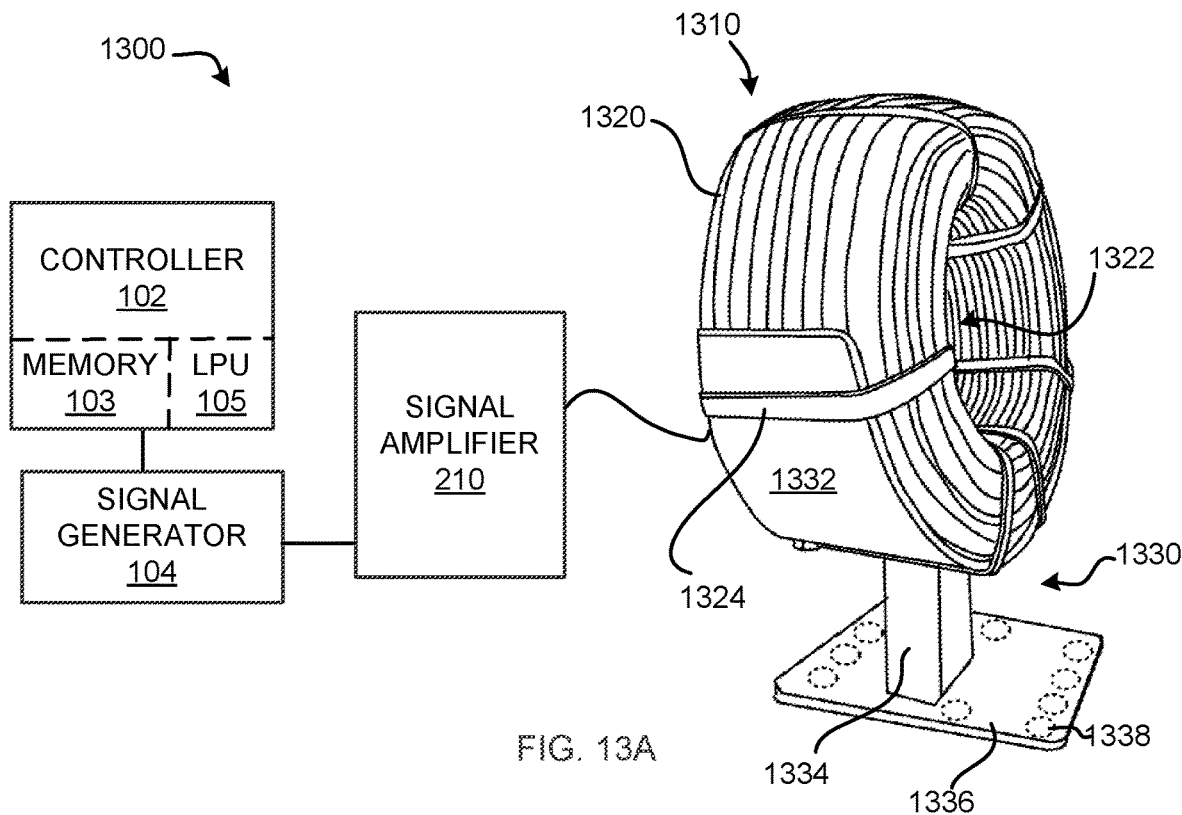
FIG. 13A is a schematic illustration of a system for treating biofilm using a coil and stand assembly in accordance with one particular embodiment of the invention.
Figure 13B:
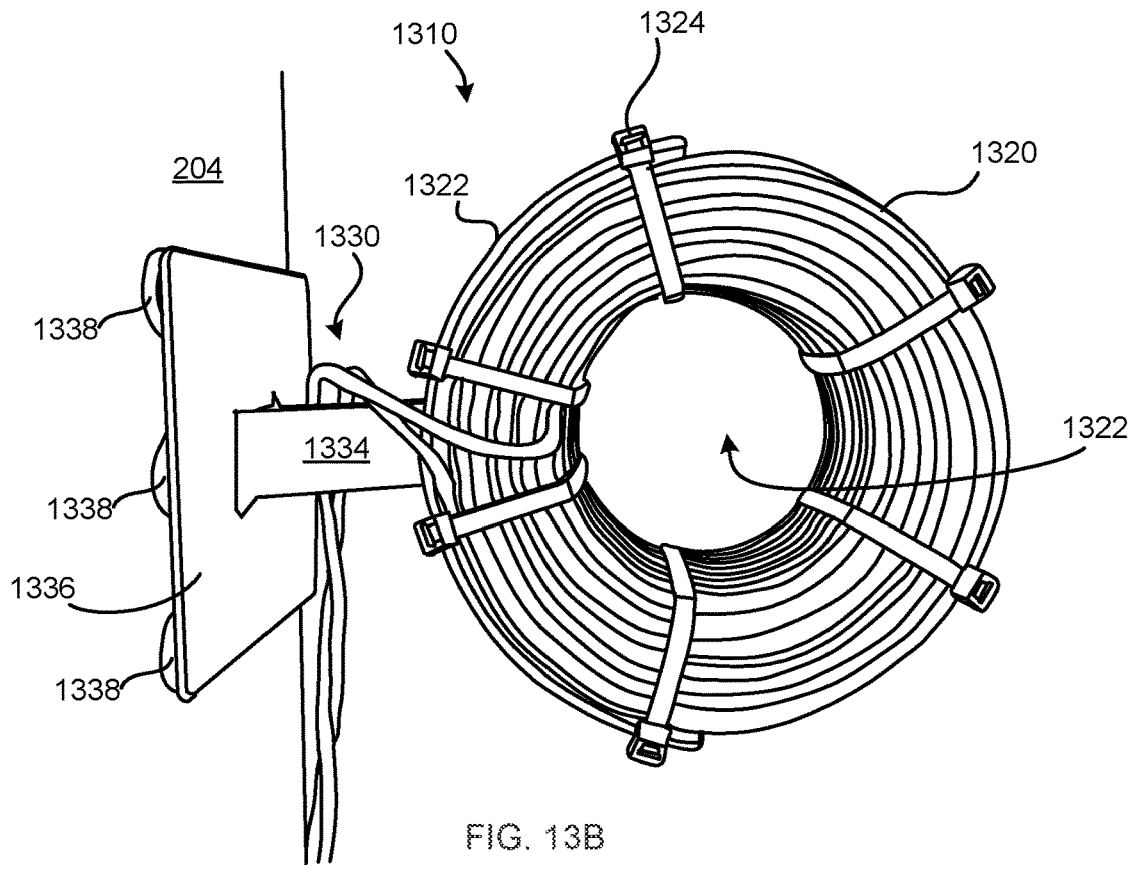
FIG. 13B is an isometric view, from the side, of a coil and stand mounted to a steel wall, in accordance with one particular embodiment of the invention.
Figure 14:
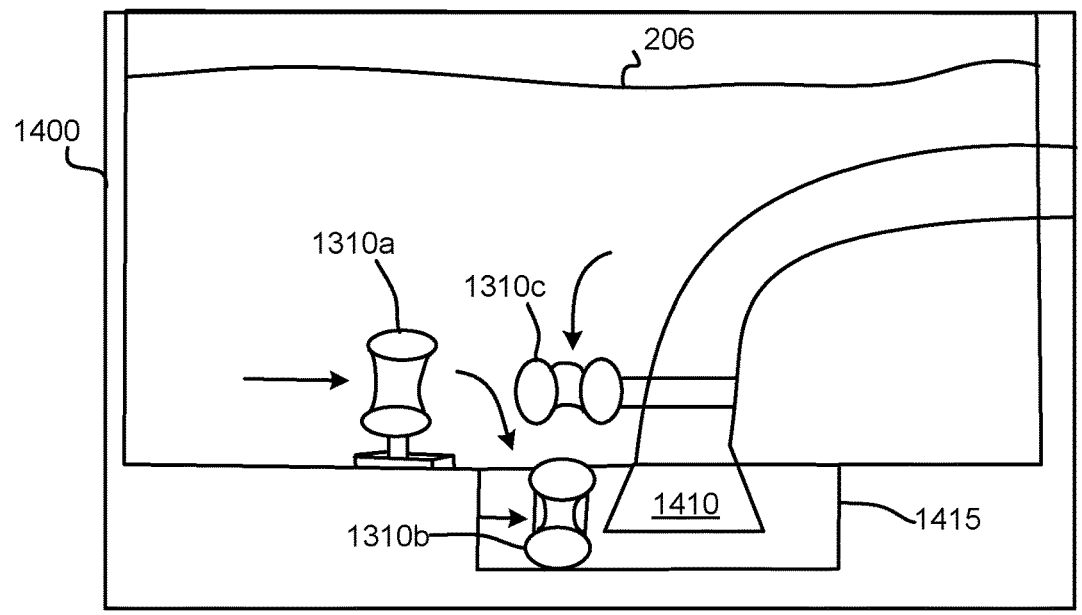
FIG. 14 is a schematic, cross-sectional illustration of a system for treating biofilm within a water reservoir and pipe system using a coil and stand in accordance with one particular embodiment of the invention.

Additionally, in accordance with one embodiment of the invention, an RF coil and stand assembly have been developed to treat biofilm within a water reservoir and/or pipe system in places where, normally, a coil would not be able to penetrate the pipe wall. Referring now to FIGS. 13A-14, there is shown one particular embodiment of an RF system 1300 for treating biofilm within a water reservoir and/or pipe system coil and stand assembly 1310. More particularly, a wire, which in one embodiment is encased in a water tight coating or cladding, is coiled about itself, forming a coil 1320 having a defined central opening 1322 through which fluid can flow. The coil 1320 is supported by a stand 1330. In one particular embodiment of the invention, the coil is secured in its shape, and to the stand 1330, by zip ties 1324 or other kinds of ties, clips or bands. The stand 1330 has a "U" shaped portion 1332 that is sized and shaped to support the coil, as illustrated. In one particular embodiment, the sides of the "U" shaped portion extend nearly half the outer circumference of the coil 1320. The "U" shaped portion 1332 is supported by a neck or stem 1334 and base 1336. In one particularly preferred embodiment of the invention, a plurality of strong magnets 1338, such as neodymium magnets, are secured to the bottom surface of the base 1336 so that the stand can be easily secured to the floor or walls of a steel tank without the need for welding in the tank. In one particular embodiment, the stand 1330 has ten magnets secured to the bottom surface thereof, for ease of installation. In an embodiment, the magnets 1338 are bolted to the base.

In use, the coil and stand assembly 1310 is clamped in front of a suction line or water intake opening and connected to at least a signal generator 104. A direct connection can be used, or the coil can be connected via a junction box (250 of FIG. 2C) located in the tank. Optionally, a signal amplifier 210 may also be provided. The signal generator 104 is controlled by a controller 102 to receive a square wave signal with a frequency that is swept from between 2,000 Hertz and 24,000 Hertz, thereby increasing the number of free water molecules present in the fluid being transported along the fluidic path through the defined central opening 1322. Thus, as water is suctioned into the an intake line or opening, most will pass through the opening 1322, and correspondingly, through an electromagnetic field induced by the coil 1320.

It is important to note that other configurations of coil can be used as the coil 1320, and supported on the stand 1330. For example, in one particular embodiment, the coil 1320 is wrapped as a toroidal, Rodin coil, having a defined opening 1322, therethrough. The magnetic field produced by a Rodin coil is particularly efficient for cleansing a fluid stream passing therethrough.

In one particular embodiment illustrated in FIG. 14, coil assemblies 1310a, 1310b and 1310c are placed within a tank 1400, proximal to a water suction line intake pipe 1410 that is suctioning water out of a well 1415 of the tank 1400. The assemblies 1310a, 1310b, 1310c are located in the fluid paths (denoted by the arrows) to the well 1415 and/or suction line 1410. More particularly, assembly 1310a is fixed, by the magnets on its base, to a floor of the tank 1400 in the fluid path to the well 1415. Similarly, the assembly 1310c is strapped, by its base, or otherwise fixed to the intake pipe 1410 in the fluid path to the well 1415. Assembly 1310b is fixed, at its base, to a wall of the well 1415. Thus, water entering the well 1415 and being suctioned into the mouth of the pipe 1410 will first pass through the defined central opening of at least one of the coil assemblies 1310a, 1310b, 1310c and correspondingly, through the field induced in the coils thereof by the signal generator (104 of FIG. 13A) before entering the intake pipe 1410.

Figure 15:
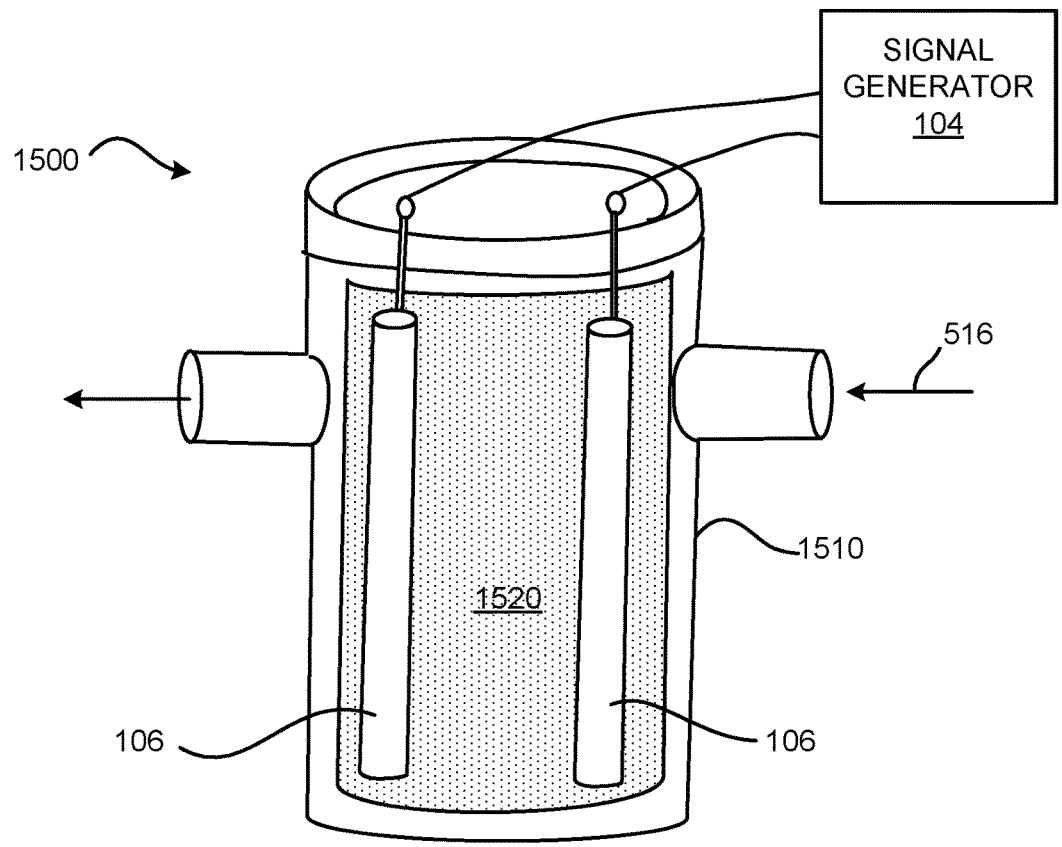
FIG. 15 is a diagrammatic view of a water filter in accordance with one embodiment of the invention.

It should be understood that systems using the emitters 106 and coils 602, described herein, can be used in other types of systems to cleanse fluids and/or objects. For example, referring now to FIG. 15, there is shown a water filter 1500 inserted in a fluid path 516. Water filter 1500 uses two emitters 106, as described herein, disposed in the housing 1510 to cleanse water passing through a bed of activated carbon filter material 1520. Signal generator 104 provides a signal of varying frequencies (as discussed herein), to sterilize water passing through the filter material, around the emitters 106, prior to the water exiting the filter 1500.

Similarly, referring now to FIG. 16, there is shown one particular embodiment of a household water filter system 1600, which uses coils 602 outside the pipe 500 to reduce the growth of biofilm and to cut down scale in the pipes 500. A frequency generator 1602, powered by a power supply 1604, is used to provide a square waveform to the coils 602, as described elsewhere herein. If desired, an emitter 106 can also be used. A vent valve 1608 is provided on the pipe 500. The entire system 1600 can be contained within a cabinet 1608 that can be located at the inlet for the household water supply.

Additionally, referring now to FIGS. 17A and 17B, there is shown one particular embodiment of an RF cleaning and sterilization system 1700 that can replace a UV filter in accordance with one embodiment of the invention. More particularly, fluid input to the system 1700 is circulated through four stages 1710, each of which includes five emitters 106, before leaving the system 1700. Fluid, such as water enters an inlet and proceeds and flows through each stage 1710. A control box (101 of FIG. 2A) operates to cycle the frequency of the emitters 106 through a range most effective to destroy the targeted bacteria, as described elsewhere herein. As with other systems described herein, the system 1700 is effective on a broad range of pathogens, including *E. coli, Giardia* and *Cryptosporidium* and is not dependent on pH or water temperature. Water flows through the system 1700 without the need for a holding tank or reaction times. Additionally, the system is chlorine free and does not produce disinfection byproducts. In contrast to UV systems, the system 1700 also has low electrical requirements.

Referring now to FIGS. 1-3, 5, 7A, 7B, 8, 15 and 17, there will now be described a method 800 for cleaning and sterilizing a volume of fluid within a fluid reservoir 200 or within an enclosed fluidic path 516 using an RF cleaning and sterilizing system 100, 100a, 100a', 100b, 100c, 100d, 1500, 1700. First, an electromagnetic wave is generated by a signal generator 104. Step 802 of FIG. 8. Such a signal may have an amplitude of between 12 Volts and 20 Volts or more, as described herein. The amplitude of the generated signal may be based on the number of emitters 106 to be used within the RF cleaning and sterilizing system 100, 100a, 100a', 100b, 100c, 100d, 1500, 1700.

In one preferred embodiment, the frequency of the generated electromagnetic wave is varied across a frequency range. Step 804 of FIG. 8. Such variation across the frequency range may be controlled via signals received from a controller 102. In some embodiments, the frequency range may be based upon the type of bacteria, virus, or other pathogen to be neutralized within the fluid. In some embodiments, for example, the frequency range may be between 3 kHz and 8 kHz to neutralize the bacteria responsible for Legionnaire's disease. In some embodiments, a larger frequency range, such as between 0 Hz and 30 kHz, or between 0 Hz and 25 KHz, may be used to neutralize a larger selection of bacteria, viruses, and other pathogen. In one preferred embodiment of the invention, the frequencies produced by the signal generator 104 during operation of the method 800 are no higher than 50 kHz. More preferably, the frequencies produced by the signal generator 104 during operation of the method 800 are no higher than 30 kHz. A comprehensive Consolidated Annotated Frequency List (CAFL) of the frequencies to which different bacteria, viruses and pathogens are susceptible is produced from "The Electroherbalism Frequency Lists" and can be found on the electroherbalism website.

The electromagnetic wave is applied to one or more emitters 106. Step 806 of FIG. 8. The number of emitters 106 may depend upon the size and configuration of the fluid reservoir 200 or the enclosed fluidic paths 516. For example, such a sterilizing system may use two emitters 106 in a hot tub, while an 80 Million gallon tank may use 6 systems having eight emitters each (i.e., a total of forty-eight emitters 106). In some embodiments, the electromagnetic wave may be applied to the emitter 106 after step 802, but before step 804, in which the frequency of the electromagnetic wave is varied.

A volume of water or other fluid is transferred into the fluid reservoir 200 or through the fluidic path 516. Step 808 of FIG. 8. Such water or other fluid may thereby be cleaned and sterilized according to the above method 800.

Referring now to FIGS. 3, 6, 7A, 7B, 9 and 16, a method 900 will be described for creating free water molecules that may then be used to reduce scale inside the pipe 500. A square waveform may be generated by a signal generator 104. Step 902 of FIG. 9. Such a square waveform may have an amplitude of about +/−5 Volts and/or +/−65 milliamps.

The frequency of the square wave is varied across a frequency range. Step 904 of FIG. 9. Such variation across the frequency range may be controlled via signals received from a controller 102. In some embodiments, the frequency range may be based upon a frequency or frequencies that may be used to separate calcium and/or calcium carbonate ions from water molecules, thereby forming free water molecules that are transported further along the enclosed fluidic path 516. A similar square waveform may also be applied to the coil 1320 of FIGS. 13A and 13B, in operation.

The square waveform is applied to a one or more sets of wire coils 319, 602, 1302 that may be wrapped or coiled around the outside surface 508 of a pipe 500, or inside a pipe or in front of an intake to a pipe (see FIG. 14). Step 906 of FIG. 9.

A volume of water is transferred along a fluidic path 516 that runs through the wrapped or coiled set of wires 602. Step 908 of FIG. 9. For example, if the coils 602 are wrapped around the outside of the pipe 500, fluid is passed through the pipe 500. For coils 1302 disposed at the intake of a pipe 500, for example, in front of a suction line, the volume of water will pass through the coils 1302 (and the resulting magnetic field) as it enters the pipe 500.

FIG. 10 is a simplified schematic diagram of one embodiment of a controller 102 that may be used to generate and transmit the instructions for the signal generator 104 to vary the frequency of the signal being generated by the signal generator 104. The controller 102 may include a computing system capable of executing one or more instruction sets. The controller 102 may include a processing unit 1000, a system memory 1002, a memory expansion slot 1004, a network interface 1006 and associated network driver 1008, and an input/output interface 1010 and associated I/O driver(s) 1012. A system bus 1014 may communicably couples various system components to the processing unit 1000. The controller 102 may at times be referred to in the singular herein, but this is not intended to limit the embodiments to a single system, since in certain embodiments, there will be more than one system or other networked computing device involved. Non-limiting examples of commercially available systems include, but are not limited to, an Atom, Pentium, or 80×86 architecture microprocessor as offered by Intel Corporation, a Snapdragon processor as offered by Qualcomm, Inc., a PowerPC microprocessor as offered by IBM, a Sparc microprocessor as offered by Sun Microsystems, Inc., a PA-RISC series microprocessor as offered by Hewlett-Packard Company, an A6 or A8 series processor as offered by Apple Inc., or a 68xxx series microprocessor as offered by Motorola Corporation.

The processing unit 1000 may be any logic processing unit, such as one or more central processing units (CPUs), microprocessors, digital signal processors (DSPs), application-specific integrated circuits (ASICs), field programmable gate arrays (FPGAs), programmable logic controllers (PLCs), etc. The system bus 1014 can employ any known bus structures or architectures, including a memory bus with memory controller, a peripheral bus, and a local bus. The system bus 1014 may take, for example, the form of a plurality of buses (e.g., data buses, instruction buses, power buses) included in at least one body.

The system memory 1002 may include read-only memory ("ROM") 1016 and random access memory ("RAM") 1018. The system memory 1002 may include a flash drive to store data and/or processor-executable instructions. In some embodiments, the system memory 1002 may include a hard disk drive for reading from and writing to a hard disk, an optical disk drive for reading from and writing to removable optical disks, and/or a magnetic disk drive for reading from and writing to magnetic disks. The system memory 1002 may include one or more sets of processor-executable instructions or software 1020, that when executed, cause the controller 102 to transmit instructions to one or more signal generators 104 to perform one or more cleaning and sterilization routines, as discussed above. Such cleaning and sterilization routines, when executed, may cause the processor 1000 to transmit a first signal or first set of instructions to the signal generator 104 via the network interface 1006. The system memory 1002 may communicate with the processing unit 1000 via the system bus 1014. Those skilled in the relevant art will appreciate that other types of computer-readable media that can store data accessible by a computer may be employed.

The memory expansion slot 1004 may be used to receive one or more types of removable media that may be used to store one or more sets of processor-executable instructions. Such removable media may include, for example, a secure digital (SD) card, a compact flash (CF) card, a universal serial bus (USB) memory "stick," or the like.

The controller 102 may include a network interface 1006 and associated network driver 1008 that enable the controller 102 to communicate with one or more communications or data networks. The network driver 1008, for example, may include one or more wireless and/or wired communication stacks that enable the controller 102 to transmit data through a communications network via the network interface 1006. In some embodiments, the network driver 1008 and network interface 1006 may enable the controller 102 to communicate with the signal generator 104. The network interface 1006 may include a wired communications port (e.g., a USB port, a game port, or other like port) and/or a wireless communications port (e.g., an antenna). Suitable communication protocols include FTP, HTTP, Web Services, SOAP with XML, WI-FI™ compliant, BLUETOOTH™ compliant, Near Field Communications (NFC) standards, cellular (e.g., GSM, CDMA), and the like. Suitable transportation protocols include TCP/IP, SCTP, DCCP, and the like.

The controller 102 may include an input/output interface 1010 and associated driver 102. The input/output interface 1010 may be electrically and communicatively coupled to input devices that may be used to receive user inputs in the form of electrical signals. Such user inputs may include, for example, selecting between a plurality of variable frequency and/or cleaning and sterilization programs stored as sets of processor-executable instructions 1020 by the system memory 1002. The input/output interface 1010 may be communicatively coupled to various devices, such as, for example, a touchscreen or touch sensitive display device that may include any type of touchscreen (e.g., a resistive touchscreen or a capacitive touchscreen). In some embodiments, the touchscreen or touch sensitive display device may present a graphical user interface, for example in the form of a number of distinct screens or windows, which include prompts and/or fields for selecting various emitters and/or cleaning and sterilization processes. The touchscreen or touch sensitive display device may present or display individual icons and controls, for example virtual buttons or slider controls and virtual keyboard or key pads which are used to communicate instructions, commands, and/or data. The input/output interface 1010 may additionally or alternatively be communicatively and/or electrically coupled to one or more additional input or output devices, for example, a microphone, speakers, an alphanumeric keypad, a QWERTY keyboard, a joystick, scroll wheel, touchpad or similar physical or virtual input device, a light emitting device such as may be used to indicate an operational status of the various components in the RF cleaning and sterilizing system 100.

Various embodiments of the devices and/or processes via the use of block diagrams, schematics, and examples have been set forth herein. Insofar as such block diagrams, schematics, and examples contain one or more functions and/or operations, it will be understood by those skilled in the art that each function and/or operation within such block diagrams, flowcharts, or examples can be implemented, individually and/or collectively, by a wide range of hardware, software, firmware, or virtually any combination thereof. In one embodiment, the present subject matter may be implemented via Application Specific Integrated Circuits (ASICs). However, those skilled in the art will recognize that the embodiments disclosed herein, in whole or in part, can be equivalently implemented in standard integrated circuits, as one or more computer programs running on one or more computers (e.g., as one or more programs running on one or more computer systems), as one or more programs running on one or more controllers (e.g., microcontrollers) as one or more programs running on one or more processors (e.g., microprocessors), as firmware, or as virtually any combination thereof, and that designing the circuitry and/or writing the code for the software and or firmware would be well within the skill of one of ordinary skill in the art in light of this disclosure.

When logic is implemented as software and stored in memory, one skilled in the art will appreciate that logic or information, can be stored on any computer readable medium for use by or in connection with any computer and/or processor related system or method. In the context of this document, a memory is a computer readable medium that is an electronic, magnetic, optical, or other another physical device or means that contains or stores a computer and/or processor program. Logic and/or the information can be embodied in any computer readable medium for use by or in connection with an instruction execution system, apparatus, or device, such as a computer-based system, processor-containing system, or other system that can fetch the instructions from the instruction execution system, apparatus, or device and execute the instructions associated with logic and/or information. In the context of this specification, a "computer readable medium" can be any means that can store, communicate, propagate, or transport the program associated with logic and/or information for use by or in connection with the instruction execution system, apparatus, and/or device. The computer readable medium can be, for example, but not limited to, an electronic, magnetic, optical, electromagnetic, infrared, or semiconductor system, apparatus, device, or propagation medium. More specific examples (a non-exhaustive list) of the computer readable medium would include the following: an electrical connection having one or more wires, a portable computer diskette (magnetic, compact flash card, secure digital, or the like), a random access memory (RAM), a read-only memory (ROM), an erasable programmable read-only memory (EPROM, EEPROM, or Flash memory), an optical fiber, and a portable compact disc read-only memory (CDROM). Note that the computer-readable medium could even be paper or another suitable medium upon which the program associated with logic and/or information is printed, as the program can be electronically captured, via for instance optical scanning of the paper or other medium, then compiled, interpreted or otherwise processed in a suitable manner if necessary, and then stored in memory.

In addition, those skilled in the art will appreciate that certain mechanisms of taught herein are capable of being distributed as a program product in a variety of forms, and that an illustrative embodiment applies equally regardless of the particular type of signal bearing media used to actually carry out the distribution. Examples of signal bearing media include, but are not limited to, the following: recordable type media such as floppy disks, hard disk drives, CD ROMs, digital tape, and computer memory; and transmission type media such as digital and analog communication links using TDM or IP based communication links (e.g., packet links).

The various embodiments described above can be combined to provide further embodiments. From the foregoing it will be appreciated that, although specific embodiments have been described herein for purposes of illustration, various modifications may be made without deviating from the spirit and scope of the teachings. Accordingly, the claims are not limited by the disclosed embodiments.

The invention claimed is:

1. A system for sanitizing a fluid in a receptacle or an object disposed in a fluid, the system comprising:
    at least one emitter disposed in said receptacle, the at least one emitter having a first end and a second end separated by a length;
    at least one reference emitter, said at least one reference emitter being of the same type of emitter as said at least one emitter;
    a signal generator electrically coupled to the at least one emitter and configured to generate an electromagnetic signal of variable frequency;

a controller communicatively coupled to the signal generator, said controller configured to cause the signal generator to generate an electromagnetic signal that varies in frequency across a frequency range; and a feedback system communicatively coupled to said controller and to said at least one reference emitter, for forwarding a signal provided by said at least one reference emitter to said controller, said controller configured to evaluate said signal to confirm a functionality of the system.

2. The system of claim 1 wherein said at least one emitter is from 12 inches to 24 inches in length.

3. The system of claim 1 wherein the frequency range varies between 0 Hz and 30 kHz.

4. The system of claim 3 wherein the frequency range varies between 0 Hz and 25 kHz in 10 milliseconds or less.

5. The system of claim 4 wherein the signal generator operably sweeps between 0 Hz and 25 kHz in a time period, the time period based at least in part on a flow rate of the fluid and the length of the at least one emitter.

6. The system of claim 5 wherein the time period is less than one third of the length of the at least one emitter divided by the flow rate of the fluid.

7. The system of claim 1, wherein the receptacle is a tank or fluid reservoir, and said at least one emitter is disposed in said tank or fluid reservoir.

8. The system of claim 7, wherein said at least one emitter is two or more emitters positioned at different location within said tank or fluid reservoir, each emitter of said two or more emitters being at least 12 inches in length.

9. The system of claim 1, wherein said at least one emitter comprises a tube including steel wool balls inside said tube.

10. The system of claim 9, wherein said tube is made from perforated stainless steel.

11. A method for sanitizing, in a system according to claim 1, a fluid in a receptacle or an object disposed in the fluid, the method comprising:
positioning the at least one emitter and the at least one reference emitter in the receptacle;
generating an electromagnetic wave with a wave frequency;
varying the wave frequency of the electromagnetic wave across a frequency range;
applying the varying electromagnetic wave as a signal to the at least one emitter; and
evaluating a signal provided by the at least one reference emitter.

12. The method of claim 11, wherein the varying step varies the wave frequency from between 0 Hz and 30 kHz within a predefined time period.

13. The method of claim 12, further comprising:
determining the predefined time period for sweeping the wave frequency of the electromagnetic wave between 0 Hz and 25 kHz based at least in part on the length of the at least one emitter and a flow rate of the fluid within an enclosed fluidic path.

14. The method of claim 11, wherein the receptacle is a tank or fluid reservoir.

15. A method for sanitizing a fluid in a tank or fluid reservoir or an object disposed in the fluid, in a system including at least one emitter disposed in said tank or fluid reservoir, the at least one emitter having a first end and a second end separated by a length, a signal generator electrically coupled to the at least one emitter and configured to generate an electromagnetic signal of variable frequency, and a controller communicatively coupled to the signal generator, said controller configured to cause the signal generator to generate an electromagnetic signal that varies in frequency across a frequency range, the method comprising:
positioning the at least one emitter in the tank or fluid reservoir;
generating an electromagnetic wave with a wave frequency;
varying the wave frequency of the electromagnetic wave across a frequency range;
applying the varying electromagnetic wave as a signal to the at least one emitter; and
placing a food item on a horizontal surface in the tank or fluid reservoir.

* * * * *